United States Patent
Higgins et al.

(10) Patent No.: US 9,037,215 B2
(45) Date of Patent: May 19, 2015

(54) METHODS AND APPARATUS FOR 3D ROUTE PLANNING THROUGH HOLLOW ORGANS

(75) Inventors: William E. Higgins, State College, PA (US); Jason D. Gibbs, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 1460 days.

(21) Appl. No.: 12/018,953

(22) Filed: Jan. 24, 2008

(65) Prior Publication Data
US 2008/0183073 A1 Jul. 31, 2008

Related U.S. Application Data

(60) Provisional application No. 60/887,472, filed on Jan. 31, 2007.

(51) Int. Cl.
*A61B 5/05* (2006.01)
*A61B 1/00* (2006.01)
(Continued)

(52) U.S. Cl.
CPC ......... *G06T 19/003* (2013.01); *A61B 2019/505* (2013.01); *A61B 2019/507* (2013.01); *G06T 2207/30061* (2013.01); *G06T 2210/41* (2013.01)

(58) Field of Classification Search
CPC .................. A61B 2019/505; A61B 2019/507; G06T 19/003; G06T 2207/30061; G06T 2210/41
USPC ................. 600/424, 425, 407, 104, 101, 114; 382/128
See application file for complete search history.

(56) References Cited

U.S. PATENT DOCUMENTS

| 4,791,934 A | 12/1988 | Brunnett |
| 5,740,802 A | 4/1998 | Nafis et al. |

(Continued)

FOREIGN PATENT DOCUMENTS

| KR | 20020041577 | | 6/2002 |
| WO | WO 2006/020792 | * | 2/2006 |
| WO | WO-2006076789 | | 7/2006 |

OTHER PUBLICATIONS

Kukuk, M. "Modeling the Internal and External Constraints of a Flexible Endoscope for Calculating its Workspace: Application in Transbronchial Needle Aspiration Guidance." Medical Imaging 2002: Visualization, Image-Guided Procedures, and Display; Proceedings of the SPIE 2002, vol. 4681, pp. 539-550.

(Continued)

*Primary Examiner* — Katherine Fernandez
(74) *Attorney, Agent, or Firm* — Gifford, Krass, Sprinkle, Anderson & Citkowski, P.C.

(57) ABSTRACT

Methods and apparatus assist in planning routes through hollow, branching organs in patients to optimize subsequent endoscopic procedures. Information is provided about the organ and a follow-on endoscopic procedure associated with the organ. The most appropriate navigable route or routes to a target region of interest (ROI) within the organ are then identified given anatomical, endoscopic-device, or procedure-specific constraints derived from the information provided. The method may include the step of modifying the viewing direction at each site along a route to give physically meaningful navigation directions or to reflect the requirements of a follow-on live endoscopic procedure. An existing route may further be extended, if necessary, to an ROI beyond the organ. The information provided may include anatomical constraints that define locations or organs to avoid; anatomical constraints that confine the route within specific geometric locations; or a metric for selecting the most appropriate route. For example, the metric may define the closest route to the ROI such that the route satisfies all applicable anatomical, device, and procedural constraints.

44 Claims, 10 Drawing Sheets

(51) Int. Cl.
*G06K 9/00* (2006.01)
*G06T 19/00* (2011.01)
*A61B 19/00* (2006.01)

(56) References Cited

U.S. PATENT DOCUMENTS

| | | | |
|---|---|---|---|
| 5,748,767 | A | 5/1998 | Raab |
| 5,765,561 | A | 6/1998 | Chen et al. |
| 5,776,050 | A | 7/1998 | Chen et al. |
| 5,782,762 | A | 7/1998 | Vining |
| 5,792,147 | A | 8/1998 | Evans et al. |
| 5,830,145 | A | 11/1998 | Tenhoff |
| 5,891,034 | A | 4/1999 | Bucholz |
| 5,901,199 | A | 5/1999 | Murphy et al. |
| 5,920,319 | A | 7/1999 | Vining et al. |
| 5,963,612 | A | 10/1999 | Navab |
| 5,963,613 | A | 10/1999 | Navab |
| 5,971,767 | A | 10/1999 | Kaufman et al. |
| 5,999,840 | A | 12/1999 | Grimson et al. |
| 6,006,126 | A | 12/1999 | Cosman |
| 6,016,439 | A | 1/2000 | Acker |
| 6,049,582 | A | 4/2000 | Navab |
| 6,083,162 | A | 7/2000 | Vining |
| 6,190,395 | B1 | 2/2001 | Williams |
| 6,201,543 | B1 | 3/2001 | O'Donnell et al. |
| 6,236,743 | B1 | 5/2001 | Pratt |
| 6,272,366 | B1 | 8/2001 | Vining |
| 6,311,116 | B1 | 10/2001 | Lee |
| 6,334,847 | B1 | 1/2002 | Fenster et al. |
| 6,343,936 | B1 | 2/2002 | Kaufman et al. |
| 6,351,573 | B1 | 2/2002 | Schneider |
| 6,366,800 | B1 | 4/2002 | Vining et al. |
| 6,442,417 | B1 | 8/2002 | Shahidi et al. |
| 6,470,207 | B1 | 10/2002 | Simon et al. |
| 6,491,702 | B2 | 12/2002 | Heilbrun et al. |
| 6,514,082 | B2 | 2/2003 | Kaufman et al. |
| 6,535,756 | B1 | 3/2003 | Simon et al. |
| 6,546,279 | B1 | 4/2003 | Bova et al. |
| 6,593,884 | B1 | 7/2003 | Gilboa et al. |
| 6,674,879 | B1 | 1/2004 | Weisman et al. |
| 6,675,032 | B2 | 1/2004 | Chen et al. |
| 6,694,163 | B1 | 2/2004 | Vining |
| 6,771,262 | B2 | 8/2004 | Krishnan |
| 6,785,410 | B2 | 8/2004 | Vining et al. |
| 6,816,607 | B2 | 11/2004 | O'Donnell et al. |
| 6,819,785 | B1 | 11/2004 | Vining et al. |
| 6,859,203 | B2 | 2/2005 | van Muiswinkel et al. |
| 6,909,913 | B2 | 6/2005 | Vining |
| 6,920,347 | B2 | 7/2005 | Simon et al. |
| 6,928,314 | B1 | 8/2005 | Johnson et al. |
| 6,947,584 | B1 | 9/2005 | Avila et al. |
| 6,980,682 | B1 | 12/2005 | Avinash et al. |
| 7,019,745 | B2 | 3/2006 | Goto |
| 7,233,820 | B2 * | 6/2007 | Gilboa ............ 600/427 |
| 7,343,036 | B2 | 3/2008 | Kleen et al. |
| 2002/0133057 | A1 * | 9/2002 | Kukuk ............ 600/101 |
| 2003/0152897 | A1 | 8/2003 | Geiger |
| 2004/0209234 | A1 | 10/2004 | Geiger |
| 2004/0252870 | A1 | 12/2004 | Reeves et al. |
| 2005/0078858 | A1 | 4/2005 | Yao et al. |
| 2005/0096526 | A1 | 5/2005 | Reinschke |
| 2005/0272999 | A1 | 12/2005 | Guendel |
| 2006/0084860 | A1 | 4/2006 | Geiger et al. |
| 2007/0092864 | A1 * | 4/2007 | Reinhardt et al. ........... 435/4 |
| 2008/0234700 | A1 * | 9/2008 | Trovato et al. ............ 606/139 |

OTHER PUBLICATIONS

Gibbs, J.D. and W.E. Higgins. "3D Path Planning and Extension for Endoscopic Guidance." Medical Imaging 2007: Visualization and Image-Guided Procedures; Proceedings of the SPIE, vol. 6509.

Kiraly, A.P., J.P. Helferty, E.A. Hoffman, G. McLennan, and W.E. Higgins. "Three-Dimensional Path Planning for Virtual Bronchoscopy." IEEE Transactions on Medical Imaging Sep. 2004, vol. 23, No. 9, pp. 1365-1379.

Mori, K., S. Ema, T. Kitasaka, Y. Mekada, I. Ide, H. Murase, Y. Suenaga, H. Takabatake, M. Mori, and H. Natori. "Automated Nomenclature of Bronchial Branches Extracted from CT Images and Its Application to Biopsy Path Planning in Virtual Bronchoscopy." Medical Image Computing and Computer-Assisted Intervention, 2005 Lecture Notes in Computer Science, vol. 3750, pp. 854-861.

Helferty, J.P., E.A. Hoffman, G. McLennan, W.E. Higgins. "CT-video registration accuracy for virtual guidance of bronchoscopy." Proceedings of SPIE 2004, vol. 5369, pp. 150-164.

Higgins, W.E., L. Rai, S.A. Merritt, K. Lu, N.T. Linger, and K.C. Yu. "3D image fusion and guidance for computer-assisted bronchoscopy." Proceedings of SPIE 2005, vol. 6016.

Asano, F., Y Matsuno, N. Shinagawa, K. Yamazaki, T. Suzuki, T. Ishida, and H. Moriya. "A Virtual Bronchoscopic Navigation System for Pulmonary Peripheral Lesions." Chest 2006, vol. 130, No. 2, pp. 559-566.

Kukuk, M. "Modeling the Internal and External Constraints of a Flexible Endoscope for Calculating its Workspace: Application in Transbronchial Needle Aspiration Guidance." Proceedings of SPIE 2002, vol. 4681, pp. 539-550.

Gibbs, J.D. and W.E. Higgins. "3D Path Planning and Extension for Endoscopic Guidance." Proceedings of SPIE 2007, vol. 6509.

Mori, K., S. Ema, T. Kitasaka, Y. Mekada, I. Ide, H. Murase, Y. Suenaga, H. Takabatake, M. Mori, and H. Natori. "Automated Nomenclature of Bronchial Branches Extracted from CT Images and Its Application to Biopsy Path Planning in Virtual Bronchoscopy." Medical Image Computing and Computer-Assisted Intervention 2005, Lecture Notes in Computer Science 3750, pp. 854-861.

Deligianni, F., A. Chung, and G. Yang. "Patient-specific bronchoscope simulation with $pq$—space-based 2D/3D registration." Computer Aided Surgery, vol. 9, No. 5, p. 215-226 (2004).

Lee, P.Y. and J.B. Moore. "Pose Estimation via Gauss-Newton-on-manifold." 16th International Symposium on Mathematical Theory of Network and System (MTNS), Leuven, 2004.

Hamadeh, A., S. Lavallee, and P. Cinquin. "Automated 3-Dimensional Computed Tomographic and Fluoroscopic Image Registration." Computer Aided Surgery 1998, vol. 3: p. 11-19.

Roberson, R.E. and P.W. Likins. "A Linearization Tool for Use with Matrix Formalisms of Rotational Dynamics." Archive of Applied Mathematics, vol. 37, No. 6: p. 388-392. Nov. 1969.

Asano, F., Y. Matsuno, T. Matsushita, H. Kondo, Yoshio Saito, A. Seko, and Y. Ishihara. "Transbronchial Diagnosis of a Pulmonary Peripheral Small Lesion Using an Ultrathin Bronchoscope with Virtual Bronchoscopic Navigation." Journal of Bronchology (2002), vol. 9, No. 2, p. 108-111.

Geiger, B., G.M. Weiner, K. Schulze, J. Bilger, P. Krebs, K. Wolf, T.Albrecht. "Virtual Bronchoscopy Guidance System for Transbronchial Needle Aspiration." Proceedings of SPIE vol. 5746 (2005).

Grimson, W.E.L., G.J. Ettinger, S.J. White, T. Lozano-Perez, W.M. Wells III, and R. Kikinis. "An Automatic Registration Method for Frameless Stereotaxy, Image Guided Surgery, and Enhanced Reality Visualization." IEEE Transactions on Medical Imaging, Apr. 1996, vol. 15, No. 2, p. 129-140.

Helferty, J.P., A.J. Sherbondy, A.P. Kiraly, and W.E. Higgins. "Computer-based System for the Virtual Endoscopic Guidance of Bronchoscopy." (believed to have been ,offered for sale, publicly used, and/or published prior to the filing date of this application).

Hopper, K.D., T.A. Lucas, K. Gleeson, J.L. Stauffer, R. Bascom, D. T. Mauger, R. Mahraj. "Transbronchial Biopsy with Virtual CT Bronchoscopy and Nodal Highlighting." Radiology Nov. 2001, vol. 221, No. 2, p. 531-536.

Maurer, C.R., J.M. Fitzpatrick, M.Y. Wang, R.L. Galloway, Jr., R.J. Maciunas, and G.S. Allen. "Registration of Head Volume Images Using Implantable Fidudal Markers." IEEE Transactions on Medical Imaging, Aug. 1997, vol. 16, No. 4, p. 447-462.

McAdams, H.P., P.C. Goodman, and P. Kussin. "Virtual Bronchoscopy for Directing Transbronchial Needle Aspiration of Hilar and Mediastinal Lymph Nodes: A Pilot Study." AJR May 1998, vol. 170, p. 1361-1364.

(56) References Cited

OTHER PUBLICATIONS

Merritt, S.A., L. Rai, and W.E. Higgins. "Real-Time CT-Video Registration for Continuous Endoscopic Guidance." (believed to have been offered for sale, publicly used, and/or published prior to the filing date of this application).

Mori, K., T. Enjoji, D. Deguchi, T. Kitasaka, Y. Suenaga, J. Toriwaki, H. Takabatake, and H. Natori. "New image similarity measures for bronchoscope tracking based on image registration between virtual and real bronchoscopic images." (believed to have been offered for sale, publicly used, and/or published prior to the filing date of this application).

Rai, L., S.A. Merritt, and W.E. Higgins. "Real-time Image-based Guidance Method for Lung-Cancer Assessment." (believed to have been offer for sale, publicly used, and/or published prior to the filing date of this application).

Sato, Y., M. Nakamoto, Y. Tamaki, T. Sasama, I. Sakita, Y. Nakajima, M. Monden, and S. Tamura. "Image Guidance of Breast Cancer Surgery Using 3-D Ultrasound Images and Augmented Reality Visualization." IEEE Transactions on Medical Imaging, Oct. 1998, vol. 17, No. 5, p. 681-693.

Schwarz, Y., A.C. Mehta, A. Ernst, F. Herth, A. Engel, D. Besser, and H. D. Becker. "Electromagnetic Navigation during Flexible Bronchoscopy." Respiration 2003, vol. 70, p. 516-522.

Shinagawa, N., K. Yamazaki, Y. Onodera, K. Miyasaka, E. Kikuchi, H. Dosaka-Akita, and M. Nishimura. "CT-Guided Transbronchial Biopsy Using an Ultrathin Bronchoscope with Virtual Bronchoscopic Navigation." Chest, Mar. 2004, vol. 25, p. 1138-1143.

Shoji, H., K. Mori, J. Sugiyama, Y. Suenaga, J. Toriwaki, H. Takabatake, and H. Natori. "Camera motion tracking of real endoscope by using virtual endoscopy system and texture information." Proceedings of SPIE vol. 4321, p. 122-133 (2001).

Stefansic, J.D., A.J. Herline, Y. Shyr, W.C. Chapman, J.M. Fitzpatrick, B.M. Dawant, and R.L. Galloway, Jr. "Registration of Physical Space to Laparoscopic Image Space for Use in Minimally Invasive Hepatic Surgery." IEEE Transactions on Medical Imaging, Oct. 2000, vol. 19, No. 10, p. 1012-1023.

Turcza, P. and M. Duplaga. "Navigation Systems Based on Registration of Endoscopic and CT-derived Virtual Images for Bronchofiberoscopic Procedures." Studies in Health Technology and Informatics, vol. 105, p. 253-263 (2004).

White, C.S., E.A. Weiner, P. Patel, and E.J. Britt. "Transbronchial Needle Aspiration: Guidance with CT Fluoroscopy." Chest 2000, vol. 118, No. 6, p. 1630-1638.

Higgins, W., W.J.T. Spyra, R.A. Karwoski, and E.L. Ritman. "System for Analyzing High-Resolution Three-Dimensional Coronary Angiograms." IEEE Transactions on Medical Imaging, Jun. 1996, vol. 15, No. 3, p. 377-385.

Brady M.L., W.E. Higgins, K. Ramaswamy. "Interactive navigation inside 3D radiological images." IEEE 1995, p. 33-40.

Higgins, W.E. and K. Ramaswamy. "Toward dynamic visualization for endoscopy simulation." IEEE 1994, p. 700-701.

Bricault, I., G. Ferretti, and P. Cinquin. "Registration of Real and CT-Derived Virtual Bronchoscopic Images to Assist Transbronchial Biopsy." IEEE Transactions on Medical Imaging, Oct. 1998, vol. 17, No. 5, p. 703-714.

Sherbondy, A.J., A.P. Kiraly, A.L. Austin, J.P. Helferty, S. Wan, J.Z. Turlington, T. Yang, C. Zhang, E.A. Hoffman, and G. McLennan. "Virtual Bronchoscopic approach for combining 3D CT and Endoscopic Video." Proceedings of SPIE 2000, vol. 3978, No. 104.

Helferty, J.P., A.J. Sherbondy, AP. Kiraly, J.Z. Turlington, E.A. Hoffman, G. McLennan, W.E. Higgins. "Experiments in virtual-endoscopic guidance of bronchoscopy." Proceedings of SPIE 2001, vol. 4321, No. 111.

Helferty, J.P. and W.E. Higgins. "Combined endscopic video tracking and virtual 3D CT registration for surgical guidance." Proceedings of the 2002 International Conference on Image Processing, vol. 2, pp. 961-964.

Higgins, W.E., J.P. Helferty, and D.R. Padfield. "Integrated bronchoscopic video tracking and 3D CT registration for virtual bronchoscopy." Proceedings of SPIE 2003, vol. 5031, No. 80.

Kiraly, A.P., J.P. Helferty, E.A Hoffman, G. McLennan, W.E. Higgins. "Three-dimensional path planning for virtual bronchoscopy." IEEE Transactions on Medical Imaging 2004, vol. 23, No. 11, pp. 1365-1379.

* cited by examiner

METHODS AND APPARATUS FOR 3D ROUTE PLANNING THROUGH HOLLOW ORGANS

REFERENCE TO RELATED APPLICATION

This application claims priority from U.S. Provisional Patent Application Ser. No. 60/887,472, filed Jan. 31, 2007, the entire content of which is incorporated herein by reference.

GOVERNMENT SPONSORSHIP

This invention was made with government support under Grant No. CA074325, awarded by the National Institutes of Health. The Government has certain rights in the invention.

FIELD OF THE INVENTION

This invention relates generally to medical imaging and, in particular, to a system and method for three-dimensional (3D) route planning and extension to assess hollow, branching organs in patients.

BACKGROUND OF THE INVENTION

Physicians routinely utilize three-dimensional (3D) medical imaging methods to assess hollow, branching organs in patients. Examples of such organs include the liver vasculature, heart vasculature, and the airways of the chest.[1-3] Examples of 3D medical imaging modalities used to examine these organs are multidetector computed tomography (MDCT) and magnetic resonance imaging (MRI).[4] Often, the physician must find a way to navigate through the organ to reach a target diagnostic region of interest (ROI). The navigation through the organ may be virtual—solely within data derived from the 3D image, or it may be by a device, such as an endoscope, moving through the organ in a follow-on live procedure.[1,3,5-7] In each circumstance, an appropriate route through the organ to the target location is often difficult to determine.

Lung cancer is the deadliest form of cancer in the United States, accounting for nearly 30% of all cancer deaths and having a five year survival rate of under 15 percent.[8] The current state-of-the-art workflow used to assess lung cancer consists of two phases: (1) acquisition and analysis of 3D volumetric medical images in the form of MDCT scans and (2) bronchoscopy.[5,9-11]

During phase 1, the physician manually scrolls through a series of two-dimensional (2D) axial-plane slices of the 3D MDCT image to identify suspect nodules and other abnormalities. Upon determining the 3D location and shape of a specific diagnostic region of interest (ROI), the physician determines an appropriate route through the airway tree—a complex branching structure—to reach the ROI. Defining such a route to suspect peripheral nodules in the chest can be especially challenging because: (1) several airway generations from the trachea need to be traversed, (2) the airway cross-sections are obliquely oriented relative to the given axial-plane data, and (3) the airway tree continually bifurcates as a route is traversed.[12-13]

During bronchoscopy, the physician must translate the mentally defined route in the static MDCT data to the dynamic video captured by the endoscope and navigate through the airway tree. Even in the best circumstances, mentally defining the 3D relationships between the endoscope, airways, and target ROI as depicted in the MDCT data and the video feed is difficult. Respiratory motion, coughing, and the inability to view ROIs situated beyond the airway walls make the task even more challenging. Previous research has shown a high degree of variability in bronchoscopy performance between physicians, confirming these difficulties.[14]

Computer-based image-analysis techniques can help ease the route-planning task. Image segmentation methods identify image voxels that belong to the airway tree.[15-18] Centerline-analysis methods determine the axial structure of the airway tree.[19-24] Together, the airway-tree segmentation and centerline-analysis computations provide inputs to 3D visualizations of the airway tree and ROIs. By interacting with different visualization techniques, a route to an ROI can be manually defined. However, even with the additional information provided by the centerline-analysis and segmentation computations, manual route definition is still a challenging task.

The difficulty of manually selecting an appropriate route is illustrated in FIG. 1, wherein route selection is based on the use of an integrated 3D medical image visualization system. The Figure shows two weighted-sum projections of the chest, with the left projection computed in the coronal plane and the right projection computed in the sagittal plane.[10] The medial axes of the airway tree, derived from an automated centerline-analysis method of Kiraly et al.,[20] and a peripheral ROI are overlaid on the projections. The 3D MDCT image size is 512×512×706 with $\Delta x = \Delta y = 0.67$ mm, $\Delta z = 0.50$ mm (case 21405.3a). A route to the ROI is manually defined by selecting one of the axial paths from the trachea to a peripheral location on the coronal projection. The route is chosen because it appears to approach the ROI in this view. However, it is seen in the sagittal view that this route is inappropriate. The airway terminates in the anterior of the chest, while the ROI is located in the posterior.

The previous example is indicative of the route-planning problem. Even with the assistance of 2D, 3D, and quantitative visualization techniques such as thin-slab visualizations, 3D airway, surface, and ROI renderings, and quantitative plots of airway measurements, manual route planning is difficult.[25-28] Centerline-analysis techniques may produce over 200 distinct paths through the major airways. As a result, choosing the best airway path is a daunting task. Furthermore, airway-tree segmentation methods sometimes miss smaller airways, which often could be the ones leading to an ROI. Thus, the extracted paths through the airways can be insufficiently defined to reach a particular ROI.

There has been a great deal of research in extracting centerlines of branching anatomical structures from 3D medical images.[19-24] The centerlines provide the physician with information that would otherwise need to be mentally extracted from the volumetric image. They define the topology of the organ and provide a set of potential routes through it. However, the complex branching organs of interest contain many unique paths. Thus, manually searching through a large number of paths to find an acceptable route to an ROI is tedious. Our methods quickly perform this search, determining those paths that provide the most promising routes to the ROI. In cases where no appropriate route exists within the paths as determined by existing centerline-analysis methods, the methods analyze the 3D medical image, augmenting the paths with the locations of previously undetected parts of the branching organ.

The most extensive research previously performed in bronchoscopic-device path planning is by Kukuk, with the goal of defining a set of parameters such as insertion depth, rotation angle, amount of tip deflection, and length of needle insertion to perform a bronchoscopic procedure.[29-31] To determine these parameters, the method precisely models the bronchoscope's configuration within the airway tree as it moves toward a pre-determined target position. The method utilizes surfaces derived from an airway-tree segmentation to determine the airway's geometric boundaries. Because the method does not utilize the 3D medical image and instead relies on the surfaces to represent the airway tree, sections of the organ may not be accurately modeled due to imperfections in segmentation techniques. Other inputs include the approximate terminal location of the endoscope within the airway tree (the route destination) and physical endoscope parameters, such as the endoscope diameter, bending radius, and length of the rigid endoscope tip. Using these inputs, the method provides the parameters required to navigate to a particular location. However, the target location is limited to be within the original airway-tree segmentation and is required to be known a priori.

A centerline determination method proposed by Austin included in its calculations the importance of approaching a target ROI "head-on."[32] The method determines paths through sparsely defined centerlines. It is able to determine the location on a discrete path that is nearest an arbitrary location along the path. The nearest discrete path location is chosen so that the path does not overshoot the target location. Our proposed methods build on this idea, determining routes to complex, multiple-voxel ROIs that may extend beyond the original centerline locations.

Similar to the method proposed by Austin, Mori et al. describe a route along an organ's medial axes to a destination that is nearest an arbitrary location in space.[33] In this method, the route is augmented with anatomical labels describing the organ segments through which it passes.

Heng et al. proposed an interactive path-generation method that requires user inputs for both the start and end points of a route. By utilizing dynamic programming, this method is able to traverse poor-quality regions in the image when determining paths. However, in regions of poor image quality or weakly defined airways, the user may be required to provide multiple "seed points" to achieve acceptable results. This method, while defining paths robustly, does not fully achieve automated route-planning.

Another method to determine bronchoscopic routes has been proposed by Geiger et al.[13] This method seeks to use the pulmonary blood vessels, which they claim are easier to detect in 3D medical images than the airways themselves, as surrogate pathways to ROI locations. The method assumes a close correlation between airway locations and vessel locations. However, the existence or accuracy of this correlation is not guaranteed.

Geiger et. al. have also proposed a visualization method that allows a physician to view the ROI projected onto the airway walls when viewed from an endoluminal location.[35] This study forgoes automated route planning, requiring the physician to know the approximate route (bronchoscope) destination, but aids in needle placement. We have used similar techniques in the past, and visualization tools presenting comparable information are incorporated into the route validation phase of our method.[10]

Approaches for virtual angiography such as the one proposed by Haigron et al. require little image preprocessing.[36] The navigation and route planning is controlled by "active vision," wherein the appearance of the scene at a particular location drives the navigation decisions of the method. In this approach, segmentation and centerline analysis are essentially done "on the fly," with the method building up the topology of the branching structure as it progresses toward a pre-defined terminal point. This method may not be able to determine adequate routes if the organ is difficult to segment, as is often the case in airway trees.

Virtual navigation and visualization of the anatomy as depicted in volumetric medical images is the topic of much research.[37-40] Often, unlike in the case of bronchoscopy where ROIs must be biopsied to determine their cellular make-up, virtual endoscopy itself is the end goal. This is especially the case in virtual colonoscopy, where the goal is to eliminate the follow-on procedure. The work of Kang et al, seeks to define a path (3D locations and viewing directions) through the colon that is not necessarily an organ centerline. Instead, the path is directed toward polyp detection.[42] The method defines paths that are optimized for the virtual fly-through of the colon. The goal is to show each section of the colon wall continuously for as long a period a time as possible so that the physician has an opportunity to detect polyps. In virtual colonoscopy and similar virtual procedures, the methods seek to best define the route to expose ROIs rather than find the best route to navigate to a specific ROI.

The work of Fujii et al. seeks to find appropriate routes for minimally invasive neurosurgery. In this method, voxels within a model brain volume are assigned local costs. These costs correspond to the detrimental effects of different surgical events, such as incisions and contact. The voxel costs are assigned according to the cumulative knowledge of neurological experts.

In summary, there has been a great deal of research that seeks to define "paths" or "routes" through various organs. These paths/routes may exist solely for virtual interrogation of the image or may be defined in a manner that is conducive for follow-on endoscopic procedures. However, there seems to be no method that finds viable paths to precisely-defined ROIs in volumetric images while taking into account the physical properties of the endoscopic device, anatomical constraints, and procedure-specific constraints, and that also allows for the extension of routes beyond the segmentation, if required.

SUMMARY OF THE INVENTION

This invention resides in methods and apparatus for planning routes through hollow, branching organs in patients to optimize subsequent endoscopic procedures. Examples of applicable organs include vasculature and the airways of the chest, though the invention is not limited in this regard and may be applied to the digestive tract, the reproductive system, ducts, and any other passages.

According to the method, information is provided about the organ and a follow-on endoscopic procedure associated with the organ. The most appropriate navigable route or routes to a target region of interest (ROI) within the organ are then identified given anatomical, endoscopic-device, or procedure-specific constraints derived from the information provided.

The method may include the step of modifying the viewing direction at each site along a route to give physically meaningful navigation directions or to reflect the requirements of a follow-on live endoscopic procedure. An existing route may further be extended, if necessary, to an ROI beyond the organ.

The information provided may include anatomical constraints that define locations or organs to avoid; anatomical constraints that confine the route within specific geometric locations; or a metric for selecting the most appropriate route. For example, the metric may devine the closest route to the ROI such that the route satisfies all applicable anatomical, device, and procedural constraints.

The information may also include the definition of the ROI, or a segmentation of the organ through which navigation will occur in either the 3D image or in the real organ with an endoscopic device. The information may include the central axis or axes of the segmented organ as well as a parametric description of the endoscopic device. The parametric description may, for example, include the diameter, flexibility, or other physical characteristics of the endoscopic device, or descriptions of ancillary devices that may be used in conjunction with the primary endoscopic device. The information may be derived through a diagnostic instrument such as a multidetector computed tomographic (MDCT) chest image.

System-level implementations of the invention are also disclosed.

DETAILED DESCRIPTION OF THE INVENTION

Figure 1:
FIG. 1 shows the difficulty of manually selecting an appropriate route in a branching organ.

We have developed methods for automated route-planning, drawing upon 3D images, that assists follow-on navigation through hollow branching organs. In our work, we focus on MDCT images of the chest wherein the goal is to navigate through the airway tree, often for the treatment and assessment of lung cancer. In this paradigm, we restrict the routes to be contained within a patient-specific model of a tubular organ such as the colon or airway tree.

This invention resides in automated techniques for 3D route planning that: (1) locate the closest paths to a target ROI and (2) extend an incomplete path, if necessary, so that it reaches the ROI. Given a 3D medical image, our methods take as input: (1) precisely defined ROIs; (2) a segmentation of the branching organ through with the endoscopic device will navigate; (3) centerlines (paths) through the segmented organ; and (4) parametric description of the endoscopic device.

We use existing methods for branching-organ segmentation and centerline extraction. Using these inputs, our methods then (1) identify the closest routes to the ROI; (2) identify the closest routes that are navigable given endoscopic-device, procedural, and anatomical constraints; (3) extend the existing paths if necessary to complete a route to the ROI; and (4) modify the viewing orientation at each site along a route to reflect a specific visualization or follow-on live procedure.

When determining the route to an ROI, we introduce parameters to account for possible endoscopic-device, anatomical, and procedure-specific constraints. To determine the route to an ROI, we find the paths that satisfy preset constraints and that are near the ROI. In some cases, the segmented organ and extracted centerlines do not provide a viable route to the target. In these circumstances, we extend the existing paths by performing a directed search from the segmented organ of interest to the ROI. The methods have been integrated into a computer-based software package. Results from human 3D computed tomography chest images illustrate the efficacy of the methods.

Methods Overview

In this section, we describe our approach to the route-planning problem, with a focus on finding routes through chest airways. We begin with a discussion of the representation of the branching organ and its medial axes, the inputs to the methods, and the outputs. We then provide an overview of our set of integrated methods.

Branching Organ and Route Representation

The determination of a route through an organ to an ROI requires a 3D gray-scale medical image I of the organ and ROI. From I, an image-segmentation routine (e.g., that of Kiraly et al.[16]) generates a binary 3D image Is that defines the organ of interest. We use the conventions of Kiraly et al. to describe the medial axes of Is[20]

Collectively, the set of all medial axes comprise a tree, $T=(V,B,P)$, where $V=\{v1, \ldots, vL\}$, is the set of view sites, $B=\{b1, \ldots, bM\}$ is the set of branches, $P=\{p1, \ldots, pN\}$ the set of paths, and L, M, and N are integers$\geq 1$. A view site $v=(s,d)$ is the data structure that discretely represents the medial axes, with s corresponding to the view site's 3D location (x, y, z), and d its orientation. The orientation contains two direction vectors: $d=(\vec{T},\vec{U})$. $\vec{T}$ is the tangential view direction and $\vec{U}$ is the up direction. A branch, $b=\{va, \ldots, vl\}$, $va, \ldots, vl \in V$, combines connected view sites between the organ's topologically significant points. Topologically significant points include the origin (root) of the organ, points where the organ bifurcates, and the terminating points. A branch must contain two and only two topologically significant points that define the beginning and end of the branch, respectively. A path, $p=\{ba, \ldots, bm\}$, $ba, \ldots, bm \in B$, contains a set of connected branches. Paths must begin at a root branch b1 and terminate at the ends of Is.

We augment these data structures with the route data structure $r=\{vA, \ldots, vD\}$, with some $v \in V$ and others new, which consists of a collection of connected view sites. The final view site along the route, vD, is the route destination, which is located near the ROI. If an adequate route is not found within the original tree, our set of integrated methods extends the definition of the organ beyond Is by appending additional view sites to the original tree. The appended view sites, together with view sites within the original tree, define a new path that terminates near the ROI. We refer to the newly-defined sites along the path as the path extension.

Figure 2:
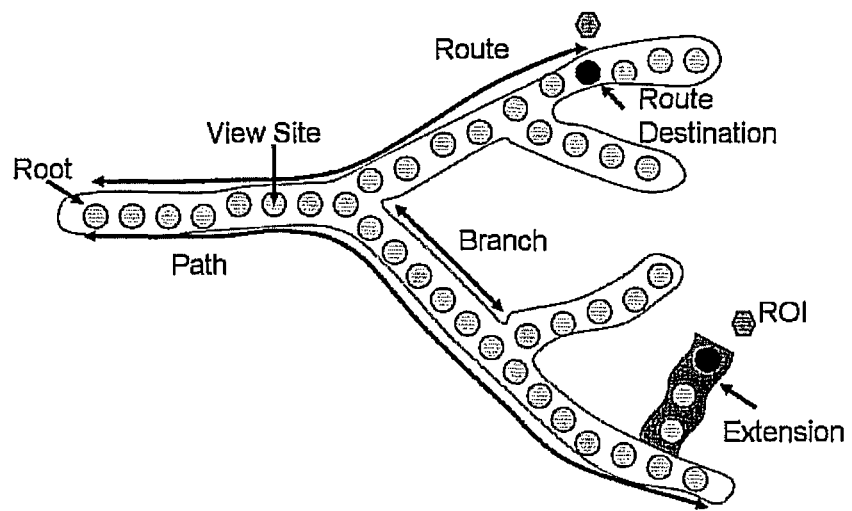
FIG. 2 is a visual depiction of different structures.

FIG. 2 gives a visual depiction of these different structures. The original organ segmentation is contained within the smooth boundary. The medial-axes tree is represented by the circular view sites within the segmentation. ROIs are shown as green hexagons. The route to the ROI at the top of the figure is entirely contained within the original tree. At the bottom of the figure, the route to the ROI requires path extension.

Inputs

The inputs required by the set of integrated methods are given below:

1. 3D medical image data of the anatomy of interest. For example, a 3D MDCT image.
2. Predefined diagnostic region of interest (ROI) in the 3D medical image data. The ROI may be defined manually, semi-automatically, or automatically. Examples of ROIs could be suspect peripheral cancer nodules, central chest lymph nodes, infiltrates, or other suspicious chest masses.
3. Pre-segmented region of the anatomy of interest. For example, the segmented airway tree.
4. Automatically precomputed tree. As an example, the tree could be the central axes of the lung airways. Each view site in the tree can optionally be augmented with anatomical labels that describe its location within the anatomy. For the lung, these labels could give lobe and segment assignments.
5. Requirements on routes that are procedure-specific. As an example, a requirement may be that the endoscope's orientation at the route destination is such that instruments can extend from the endoscope's working channel toward the ROI.

6. Dimensions and mechanical bending properties of an endoscope. The route computation may use endoscope constraints for computing feasible trajectories of a real endoscope for later interventional endoscopy.
7. Anatomical requirements. An example of an anatomical requirement may be that candidate routes do not terminate at a location and orientation where the interventional endoscopic procedure may puncture major vessels or other sensitive anatomical regions.

Outputs

Figure 3:
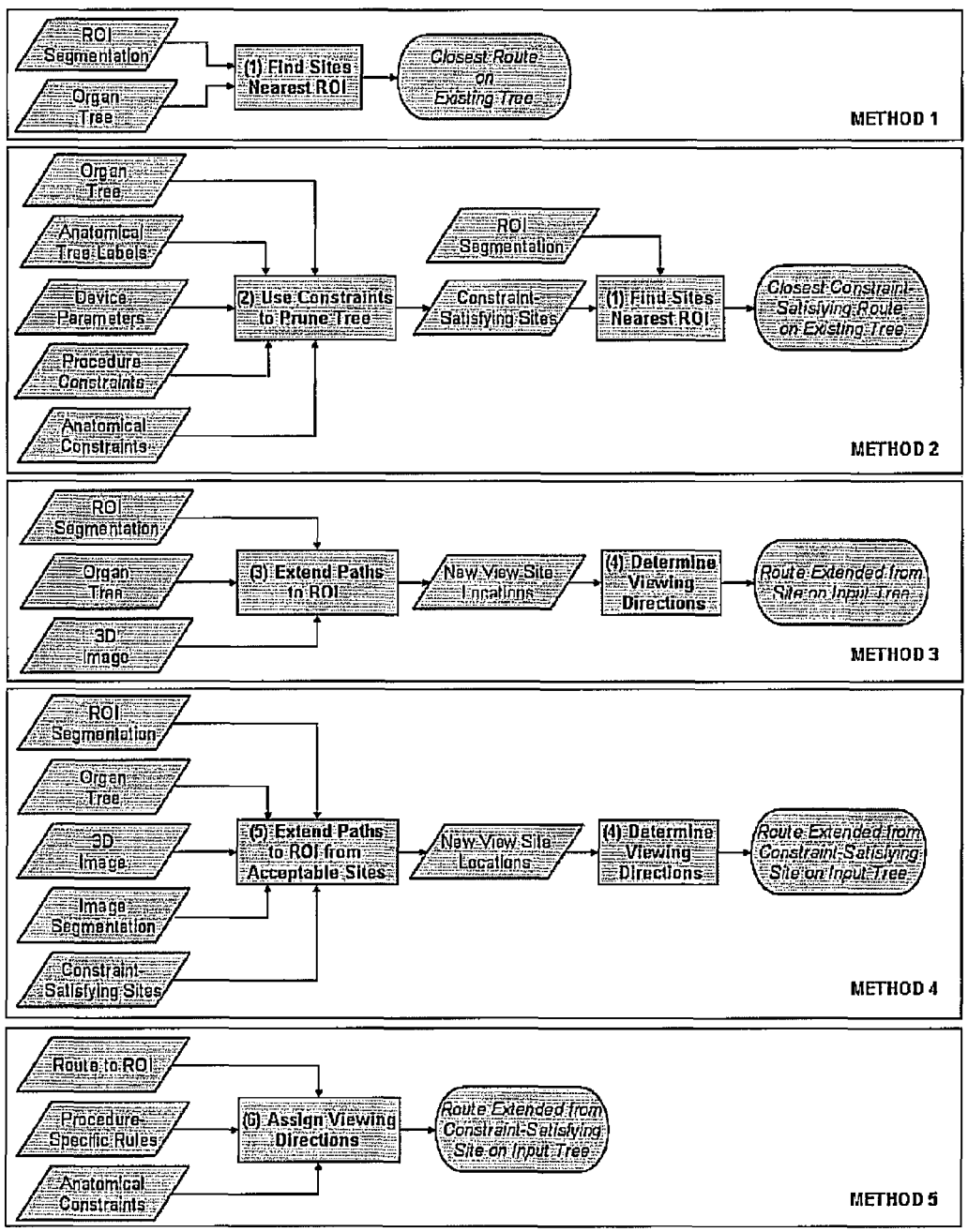
FIG. 3 is a graphical representation of the set of integrated methods for automated route planning, including the inputs, algorithms, and outputs of each method.

The set of integrated methods outputs the N closest routes to the ROI. Each route consists of a sequence of view sites within the 3D medical data. A route begins at the base of the anatomy of interest, such as the trachea for the airway tree, and concludes as close to the ROI surface as possible. The viewing directions along the route can optionally be modified so that each view site is oriented as it would be in a live follow-on procedure. A graphical representation of the set of integrated methods for automated route planning, including the inputs, algorithms, and outputs of each method is given in FIG. 3. The inputs to the algorithms of each method are given in parallelograms. The algorithms of each method are contained in rectangles. The enumeration of the algorithms is consistent with their presentation later in this section. The rounded shape at the right of each method gives the method's final output.

The Integrated Methods

This section provides an overview of the set of integrated methods. Specific algorithmic and mathematical details for each method are presented below. The objective of each component is summarized as follows:

Method 1: Determine the routes that are closest to the ROI. Find the routes contained within the input tree, T, with destinations nearest the ROI.

Method 2: Find the route that is closest to the ROI and also satisfies device, procedural, and anatomical constraints. Find the routes contained within T that are navigable for a particular device, terminate at acceptable locations and have destinations nearest the ROI.

Method 3: Find undetected paths. If the closest routes contained within T do not adequately reach the ROI, perform a directed search for undetected segments of the organ of interest within I.

Method 4: Find undetected paths near constraint-satisfying locations. Perform a directed search for undetected segments of the organ of interest from locations that satisfy device, procedural, and anatomical constraints.

Method 5: Determine procedure-appropriate viewing directions. Compute appropriate navigation directions at each view site along the determined route to reflect the procedure to be performed.

The remainder of the section provides more detail for each of the methods.

Method 1: Stay Within the Original Tree

This method finds the routes that are closest to the ROI, with the route search restricted to the set of view sites V in the input organ tree T. The closest path to the ROI pc is found first. The route destination vD is the view site on pc that is nearest the ROI. In many cases, this simple method yields acceptable routes with minimal computational complexity. To better the chances of finding an acceptable route, multiple routes are found. The method outputs the N closest routes, each with destinations on unique tree components: view sites, branches, or paths.

To find the closest routes, the distance from each 3D view site to the ROI is determined. The ROI, like the paths, is represented by a collection of discrete 3D points (voxels) in space. The method finds the ROI voxel that has the smallest Euclidean distance to each discrete viewing site. The distance calculation accounts for the anisotropic nature of many 3D volumetric medical images.

Each view site, containing information about the branch and path to which it belongs and the minimal distance to the ROI, is pushed onto a priority queue. The N closest sites are found by popping values off the priority queue in ascending distance from the ROI until N sites are found on unique segments. For performance reasons, distances are calculated only for those voxels on the ROI surface. The procedure for determining routes in this manner is outlined in Algorithm 1.

---

Algorithm 1: Closest Routes. Procedure for finding the N closest routes, each with destinations in unique tree components.

Data: Organ tree T, list of ROI voxels;
Result: Ordered list of closest routes;
Forall ROI Voxels do
| Remove from consideration all ROI voxels not neighbored on all sides by ROI voxels;
end
forall View sites in the organ tree T: $v_i$, (I = 1, ..., L) do
| forall Considered ROI voxels do
| | Compute distance to view site $v_i$;
| | if Current distance is less than minimum distance then
| | | Set minimum distance to current distance;
| | end
| end
| Push minimum distance and path information onto priority queue;
end
while N view sites on different tree components not found do
| pop closest item from priority queue;
| if Popped view site on previously unseen tree component then
| | Add view sites from root to the popped view site to the ordered output list;
| end
end

---

Method 2: Satisfy Additional Physical Constraints

The absolute closest routes found by Method 1 may yield results that are suboptimal for either virtual inspection of the 3D data or possible follow-on live procedures. The closest route destinations are often located such that the ROI is nearly at a right angle to the tangential view direction at the route destination. As such, the ROI may not be visible in virtual techniques or reachable by tools that extend straight out of the tip of the endoscopic device. In other cases, the route destination may be unreachable by endoscopic devices if it is located beyond organ constrictions or if the route has too great a curvature. To alleviate these issues, this method builds on Method 1 by requiring that candidate routes satisfy constraints related to the physical characteristics of the endoscopic device used, the procedure to be performed, and the anatomy. These restrictions include:

1. Endoscope Diameter

All view sites along an acceptable route must be above a minimum diameter threshold. If the procedure requires an endoscopic device of a certain size be inserted into the organ, this constraint ensures the device can fit within the organ along the entire route.

2. Branching Angle

Every view site along an acceptable route must have a branching angle less than or equal to the branching angle threshold. If the procedure requires an endoscopic device of a certain flexibility to be inserted in the organ, this constraint ensures that the device can bend through the route.

3. ROI/View Site Location Geometry

A viable route destination is one in which a sufficient fraction and/or minimal volume of ROI voxels lie within the "diagnostic field of view." If an endoscopic device needs to interact with the ROI (such as a needle biopsy), this constraint ensures that the device approaches the ROI in such a manner that the interaction is possible.

4. Anatomical Restrictions

The route destination should be at an appropriate location within the organ. For instance, a constraint on bronchoscopic procedures may be that the destination be at a location and have an orientation that precludes puncturing major blood vessels. Another constraint may be that the destination is located in the same lobe of the lung as the target ROI. If the procedure requires a needle or other type of tool to interact with the ROI, the latter constraint prevents puncturing a lobe of the lung when extending the tool from the route destination to the ROI.

Figure 4:
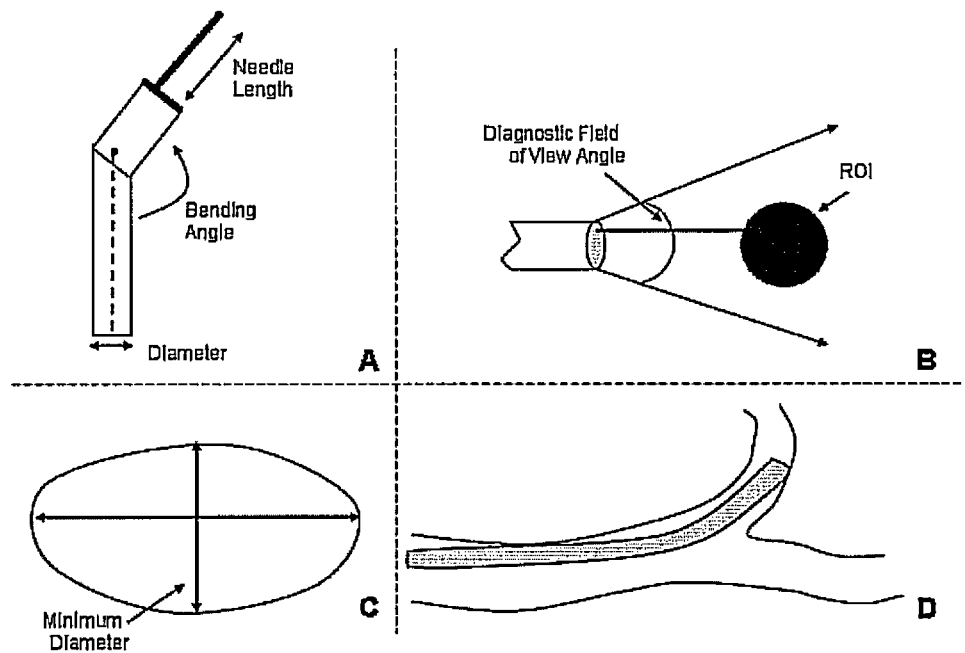
FIG. 4 shows some device and procedure-specific constraints.

FIG. 4 illustrates some device and procedure-specific constraints. Section (A) shows a simple model of the endoscope tip. The three most important characteristics of the device that determine its ability to reach a specific route destination are its diameter (it may not be able to fit past constrictions or in small peripheral locations of the organ), its bending angle (it may not be able to negotiate through sharp turns) and the length of the tool that extends out of the device's working channel. The length of the tool determines how close routes must be to the ROI. Section (B) illustrates the need to approach the ROI "head on," which is quantified by a diagnostic field of view, located at the endoscope tip. Section (C) shows a cross section of the branching organ. The organ is not necessarily cylindrical, especially at bifurcation regions. As such, the "minimum diameter" gives a measure of whether the endoscope can fit at a particular location. Finally, section (D) shows the endoscope (blue) at a location between branches with a large branching angle. If the endoscope is not flexible enough, it may not be able to move through these high-curvature regions.

Algorithm 2 outlines the procedure to determine candidate constraint-satisfying route destinations. The output of this algorithm becomes the input to Algorithm 1 which then finds the N closest routes, each with destinations on different tree components.

---

Algorithm 2: Sites Meeting Constraints. Procedure for eliminating view sites which are inaccessible given device and anatomical constraints, or have orientations relative to the ROI that are unacceptable for performing a specific procedure. The view sites that remain after these calculations are candidate route destinations.

---

Data: Set of view sites V in organ tree T, list of ROI voxels;
Result: Set of candidate route destinations C, with C ⊆ V, that meet constraint restrictions;
Set C to V;
forall Unique input paths: $p_i$, (I = 1, . . . , N) do
| forall View sites: $v_j$, (j = 1, . . . , M) on $p_i$ do
| | if View sites $v_j$ does not meet anatomical restrictions then
| | | Remove view site $v_j$ from output set C
| | else
| | | if diameter of $v_j$ less than minimum allowed OR branching angle greater than maximum allowed then
| | | | Remove view site $v_j$ and all view sites below it (all $v_x$ on $p_i$ such that j ≤ x ≤ M) from output set C;
| | | else
| | | | Set acceptable ROI count to zero forall ROI Voxels do
| | | | | if Angle between ROI voxel and $v_j$ less than minimum angle then
| | | | | | Increment ROI count;
| | | | | end
| | | | end
| | | | if ROI count not above absolute/fractional threshold then
| | | |   Remove $v_j$ from output set C;
| | | | end

---

Algorithm 2: Sites Meeting Constraints. Procedure for eliminating view sites which are inaccessible given device and anatomical constraints, or have orientations relative to the ROI that are unacceptable for performing a specific procedure. The view sites that remain after these calculations are candidate route destinations.

---

| | | end
| | end
| end
end

Method 3: Extend Existing Paths to ROI Neighborhood

In some circumstances, the set of paths in the input tree may not yield routes that adequately reach the ROI. Due to imperfections in the 3D images and variations in patients' conditions, segmentation procedures may not be able to completely define the organ of interest. Because the centerline-analysis methods extract the organ's tree from the organ segmentation, imperfections in the segmentation result in an incomplete tree. A more detailed explanation of the necessity of expanding the tree beyond what is captured by centerline-analysis methods to find appropriate routes to ROIs and the mathematical details of this method are presented elsewhere herein.

In cases where the existing paths are inadequate, this method extends the paths toward the ROI surface. A view site in the extended path may be a member of the original tree ($v \in T$) or the extension ($v \notin T$). Extensions are computed by comparing an individual voxel's local appearance to that of the organ of interest. Each voxel is assigned a cost, with low costs assigned to those voxels whose appearance is similar to the organ and high costs assigned to voxels who do not look like the organ. A path extension is found by searching for a low-cumulative-cost set of voxels that lead from the ROI to the existing segmentation. The local costs are determined using the following criteria:

1. Gray-scale (HU) Value

Voxels within an airway should have low HU values corresponding to air.

2. Local Valley Behavior

The voxels within an airway should be within a local maxima, due to the larger HU values of surrounding airway walls.

Each voxel in the volumetric image is represented as a vertex in a directed graph. Directed graph edges connect each voxel to its 26 neighbors, with edge weights E(M, N) from voxel M to its neighbor N determined by the local vertex cost scaled by the Euclidean distance between voxels (vertices).

The first step of the method is to dilate the ROI. The amount of dilation corresponds to the distance an extended path may terminate from the ROI. Because ROIs often do not lie within the airways, ROI expansion provides an opportunity for the ROI to intersect previously undetected airways.

In a manner similar to others previously proposed, Dijkstra's algorithm determines the minimal cumulative-cost set of 26-connected voxels from the dilated ROI to the existing airway tree.[34,43-45] The algorithm starts at a location on the dilated ROI, whose voxels have zero local cost. It then iteratively expands out from the vertex with lowest cumulative cost, summing the edge weight between the lowest cumulative-cost vertex and each connected vertex. The connected vertex's cumulative cost is set as this value unless the connected vertex has a lesser previously-determined cumulative cost. The algorithm keeps track of the edges and vertices traversed to get to each expanded location. These edges and vertices are the lowest-cost connected set of voxels from the ROI to a given location. Expansion halts when the vertex to be expanded is on one of the existing 3D paths. See Algorithm 3.

---

Algorithm 3: Extend Paths to ROI. Procedure for extending a path to the vicinity of an ROI. The algorithm uses Dijkstra's algorithm to traverse a weighted, directed graph derived from the 3D medical image. This algorithm returns a set of connected voxels (3D locations) that extend from the existing tree to a terminal location near the ROI.

---

Data: 3D medical image I, set of ROI voxels, organ tree T;
Result: Lowest-cost connected-set of 3D voxel locations connecting ROI to a path in T;
forall Voxels in ROI that are not completely surrounded by other ROI voxels do
| Add to ROI definition those voxels not already contained in ROI and within neighborhood distance;
end
Choose a location L on ROI to begin, set cumulative cost at L to zero, back pointer to nothing;
Push L onto priority queue;
while Location of minimum cumulative cost voxel M in priority queue not on a path do
| Remove M from priority queue;
| forall 26 Neighbors of M not previously placed in queue do
| | if Cumulative cost of current neighbor not previously set then
| | | Set current neighbor N's cumulative cost to M's cumulative cost + E(M,N) and back pointer
| | | of N to M;
| | else
| | | if Cumulative cost to M + E(M,N) is less than current cumulative cost to N then
| | | | Update cumulative cost of N to (M cumulative cost + E(M,N) and back pointer to N to
| | | | M;
| | | end
| | end
| end
end

---

The path extension of Algorithm 3 is often jagged, which is usually inconsistent with the smooth underlying anatomical structures. Furthermore, the connected set of 3D locations output by Algorithm 3 lack viewing directions. These concerns are addressed by fitting a set of 3D lines to the points. The 3D lines well-approximate short, low-curvature peripheral branches. Because the path extension may traverse multiple underlying anatomical branches, multiple 3D line segments are fit to the voxels.

Combinations of voxels in the connected set define end points of potential line segments. The set of line segments with the best cumulative "line-fit score" is accepted as the solution. The connected set of voxels is projected onto these line segments, with the tangential viewing directions pointing away from the existing path locations and toward the ROI. The up viewing direction is projected from the voxel located on the original centerline to each successive voxel toward the ROI. These steps are detailed in Algorithm 4.

---

Algorithm 4: Smooth Path Extension, Determine Viewing Directions. Procedure for smoothing the 3D path extension generated by Algorithm 3. In this algorithm, the 3D locations of view sites along the extended path are smoothed and viewing directions are assigned.

---

Data: Connected set of 3D locations, connecting view site on existing path;

Result: Smoothed Set of view sites with associated viewing directions;

Set best line fit score to ∞ ;

Forall Combinations of K line segments, whose endpoints are voxels within the connected set do

| if Current combination's line fit score less than best line fit score then

| | Set line fit score to current score;

| | Retain current endpoints;

| end

| forall Voxels in connected set, in order, starting with voxel added last in Algorithm 3 do

| | Add to output list 3D location projection;

| | of voxel onto retained line segments;

| | if First voxel on connected set then

| | | Project up viewing direction $\vec{U}$ from connecting view site on existing path;

| | else

| |    Project $\vec{U}$ from previous location

| | end

| | Set tangential viewing direction vector $\vec{T}$ along retained line segment;

| end end

---

Method 4: Satisfy Physical Constraints and Incorporate Path Extension

This method is a hybrid of Methods 2 and 3 wherein the path extension procedure of Method 3 is modified so paths are extended from those locations that satisfy the device, procedural, and anatomical constraints. As such, the endoscopic device can reach at least the beginning point of the extension.

To determine this path extension, the inputs and outputs of Method 2 are used as inputs to Method 4. Voxels in the segmentation Is are eliminated from consideration if they are closer to inaccessible view sites than accessible view sites. The distances required to make this determination are efficiently computed using the distance transform with a Euclidean distance measure.[46] Starting with those view sites that remain after Method 2, the method incrementally finds the distance from each view site to each voxel in Is. This process stops once the only voxels whose distances have not been calculated are at a distance that is at least as great as the diameter of the largest airway in Is.

The process is repeated for the inaccessible view sites, keeping track of all voxels added who have not had distances set or have a distance from an eliminated view site that is less than the distance set by the previous pass. These voxels must not be contained within path extensions. Using the output of this method, the local vertex costs of Method 3 are set to values that are effectively infinite for the black-listed voxels so that the path extensions will not pass through them. With this modification, path extensions are found using the procedure described in Method 3. The procedure to determine the black-listed voxels is outlined in Algorithm 5.

Method 5: Incorporate Procedure-Specific Navigation Directions

The methods presented thus far, as well as previously proposed centerline-analysis methods, do not necessarily give physically meaningful navigation directions. As an example, it may be desirable for the navigation directions to reflect accepted bronchoscope orientations at locations along a route. Typically, the navigation directions are chosen so that the tangential viewing direction (the direction in which the view site is looking) faces toward the end of a branch. Because most endoscopic devices are tubular objects within larger tubular organs, they are generally oriented in the direction of the organ. However, since the endoscopic devices are free to rotate, the viewing directions must also define the relative "up" direction at each view site. Generally the up vector, which quantifies this up direction, is arbitrarily chosen. However, in endoscopic procedures, such as bronchoscopy, there is often an accepted practice for the rotation of the endoscopic device so that the physician is able to maintain a sense of 3D orientation throughout the procedure and smoothly navigate along a specific route. This method adds a refinement to the routes derived by Methods 1-4 that assigns practical, useful directions to the route view sites.

Viewing directions are assigned to reflect live bronchoscopy standard practices. An example of rules used to orient the bronchoscope is given below. In this procedure, directions are determined in three different ways:

1. Anatomically Accepted Standard Positions. During the first few airway generations, the bronchoscope is oriented in standard positions depending on its location within the anatomy.

---

Algorithm 5: Extensions From Acceptable Locations. Procedure for determining the set of black-listed voxels so that a path extension does not connect to inaccessible regions of the organ tree.

---

Data: Original tree T, pruned tree that satisfies constraints $T_P$, organ segmentation $I_s$;
Result: Set of black-listed (eliminated) voxels E through which the path-extension cannot pass;
forall View sites meeting constrains ($v_i \in T_P$) do
| Push into priority queue with distance of 0;
| Set view site location as visited with nearest centerline location pointer as itself;
end
while Distances popped from top of queue are less than maximum centerline diameter do
| Determine distance from original view site location to each of 26 neighbors in $I_s$;
| if Neighbor distance has not been computed or distance from original view site to popped voxel is less
| than popped voxel's current distance then
| | Set neighbor's pointer to popped view site's original location;
| | Set distance of neighbor from pointed to location;
| | Push neighbor on priority queue;
| end
end
Flush the queue;
forall View sites not meeting constraints ($v_I \in (T \setminus T_P)$) do
| Push into priority queue with distance of 0;
| Set view site location as visited with nearest view site location pointer as itselt;
end
while Distances popped from top of queue are less than maximum view site diameter do
| Determine distance from original view site location to each of 26 neighbors in $I_s$;
| if Neighbor distance has not been computed or distance from original view site to popped voxel is less
| than popped voxel's current distance then
| | Set neighbor's pointer to popped view site's original location;
| | Set distance of neighbor from pointed to location;
| | push neighbor on priority queue;
| end
end
forall Voxels in segmentation $I_s$ do
| if Voxel points to view site not meeting constrains then
| | Add voxel to E
| end
end 2. Orient the Route Up in Periphery. As the bronchoscope moves toward the lung periphery, there are no longer standard orientations linked to specific locations in the anatomy. Instead, if a "sharp" turn is required at a bifurcation the endoscope is rotated so that the next branch along the route is located at the top of the scene.

3. Orient Toward ROI at Route Destination. The bronchoscope is oriented so that the endoscopic tool can extend from it to interact with the ROI at the route destination. Because the tool extends from one side of the bronchoscope (not the center), the orientation is such that the ROI center of mass and the endoscopic tool are located in the same portion of the view.

Viewing directions that reflect these rules are determined with knowledge of the geometry and anatomical make-up of the route. If a viewing site is near the end of a branch or the route destination, its orientation is modified to reflect the desired orientation going into the next branch or the destination. The modifications happen gradually over several view sites so the transitions are smooth and reflective of how the device moves. Algorithm 6 describes this process.

---

Algorithm 6: Route-Specific Viewing Directions. Procedure for determining viewing directions along a route for a specific endoscopic procedure.

---

Data: Organ tree T, route r, target ROI;
Result: Appropriate viewing directions along route r;
Forall View sites along r: $v_i$, (I = 1, ..., D) do
| Determine tangential direction $\vec{T}$ ;
| if First view site on route ($v_f$) then
| | Set initial up direction $\vec{U}$ ;
| end
| | Project $\vec{U}$ from previous view site;
| end
| if View site within N view sites of end of current branch then
| | if Anatomical rules exist for entering next branch then
| | | Determine proper up viewing direction entering next (child) branch $\vec{U}_c^*$ ;
| | else
| | | Determine $\vec{U}_c^*$ using general rules;
| | end
| | Blend current site's $\vec{U}$ with $\vec{U}_c^*$ ;
| end
| else if View site is within M view sites of route destination $v_D$ then
| | Determine appropriate orientation $d_D$ at $v_D$;
| | Blend current orientation, $d_C$, with $d_D$;
| end
end

---

Method Detail and Implementation

Method 1: Stay within the Original Tree

This method gives a route that stays completely inside a known, previously segmented airway. This implies that an endoscope, if small enough and flexible enough, can follow the route. This route does not necessarily completely reach the ROI, but a needle could perforate the airway wall to biopsy the ROI.

Rather than finding a single route that is the absolute closest to the ROI, the method provides the user with the set of N closest routes. However, the N absolute closest destinations will often be neighbors of one another. If the closest route destination is located on a path that yields an unacceptable route, its neighbors on the same path will likely determine unacceptable routes as well. Therefore, the method returns the N closest routes, each with destinations on unique tree segments: view sites, branches, or paths.

Method 2: Satisfy Additional Physical Constraints

This method gives a physically traversable route, via the endoscope, for reaching the ROI during a live procedure.

Details about the parameters and restrictions used are provided below:

1. Endoscope Diameter

Devices of a given diameter may not reach all parts of the airway tree without causing harm to the patient. On a valid route, all of the view site locations between the route origin and destination are at least as wide as the diameter of the endoscopic device. Airways, while being tubular structures, in general do not have circular cross sections. This is especially true in the case of stenosed airways and at bifurcations. Whether an endoscope can fit at a given view site is therefore determined by the minimal "diameter" of the cross-section of the view site.

2. Branching Angle

Endoscopic devices have a limited amount of flexibility. Therefore, the device may not be able to navigate through sharp turns. As the sites along any one particular branch tend to have little curvature, the most problematic regions are those in the transition from one branch to another. The branching angle formed between consecutive branches accounts for the flexibility constraints. By definition, locations on the same branch have a branching angle of zero.

3. ROI/View Site Location Geometry

The view sites nearest the ROI, even those on separate branches or paths, may be impractical for performing specific procedures. Many procedures require the route to approach an ROI "head-on." Quantitatively, the angle formed between the view site and voxels in the ROI and the tangential viewing direction should be small. By doubling the maximum angle allowed between the tangential viewing direction $\vec{T}$ and the direction formed by the vector connecting the ROI location to the view site location, a component of the "diagnostic field of view" is defined. This "diagnostic field of view" is a cone whose tip is located at the view site, is oriented along $\vec{T}$, and the aforementioned angle defines the angle between the sides of the cone. A valid route destination is therefore one in which an acceptable amount (either fractional or absolute, as specified by the user) of ROI volume lies within the cone. Fractional ROI volume is determined by the ratio of the number of ROI voxels that lie within the cone to the total number of ROI voxels. Absolute ROI volume is determined by summing the number of ROI voxels that fall within the cone and scaling the result by the anisotropic voxel dimensions.

4. Anatomical Restrictions

Often, anatomical restrictions dictate where a route should terminate. In many circumstances it is required that route destinations not be located near major blood vessels or other sensitive regions to minimize the risk of harm to the patient. This type of anatomical restriction indicates regions where the route should not terminate. Conversely, restrictions may dictate where routes should terminate. As an example, the ROI and route destinations may be required to be within the same lobe of the lung. The motivation for this requirement is to prevent lung perforation or other damage during a procedure (such as a biopsy). The anatomical information for the ROI, such as the lobe in which it is located, is assigned when it is segmented. Identification of the major airways and other airway-tree anatomical labeling tasks can be determined by automated techniques.[33,47,48]

Method 3: Extend Existing Paths to ROI Neighborhood

The routes determined by Method 1 may fail to adequately approach the ROI because Method 1 utilizes paths derived from a global segmentation of the branching organ. Airways appear in MDCT images as dark voxels with nominal Hounsfield Unit (HU) values of −1000 surrounded by the brighter airway wall with correspondingly larger HU values. Segmentation methods try to find all of the voxels contained within valid airways. However, efficient segmentation of the entire branching structure is a difficult task due to image noise, partial-volume effects, and other image artifacts.

Our method utilizes input segmentation methods that are designed to capture as much of the airway tree as possible without "leaking" outside of airways into the rest of the lung. For a route-planning method, leakage is more troublesome than not detecting some airways as routes may be proposed that navigate through unreachable locations. A consequence of conservatively defining the airway tree is that although input segmentations have very low false-positive rates (classifying non-airway voxels as airway voxels), they may exhibit relatively high false-negative rates (not correctly identifying airway voxels). The rates of false-negatives are especially high in small-diameter peripheral branches where the airway wall is thin and the few voxels located within the airway are easily corrupted by partial-volume effects—wherein a voxel's HU value is averaged when it straddles unlike types of matter such as the airway wall and air—and noise. Due to this high rate of false-negatives, path extension is often required.

Dilation of the ROI prior to the extension gives the ROI the opportunity to intersect the organ of interest. Without this dilation, the path extension would have to jump out of the previously undetected segments of the branching organ and eventually intersect the ROI. The voxels encountered as the extension bridges the gap between the true underlying organ and the ROI can have a significant impact on the final lowest-cost path. In dilating the ROI by an appropriate amount, as determined by the size of the ROI, the procedure performed, and the medical instruments to be used during the procedure, these problems are mitigated.

Voxel Cost Determination

The local cost determination is application-specific. For instance, the local appearance of pulmonary vessels is quite different than pulmonary airways. Blood vessels are more homogeneous than airways and are thus easier to detect. Because we are interested in finding airways, the following cost measures are tailored accordingly. However, any locally-determinable quantification of the appearance of the organ of interest could be used instead.

Local airway costs are assigned such that voxels whose local appearance is indicative of belonging to an airway are assigned low costs. Likewise, those voxels who do not have the local appearance of an airway are given high costs. Voxels that belong to the dilated ROI are assigned zero cost. Using the qualitative properties of airways previously described, the quantitative cost of a voxel V at 3D location $X=[x,y,z]^T$ is denoted as $C(X)$. This cost is determined as:

$$C(X) = \begin{cases} 0, & \text{if } X \in ROI_{dilated} \\ L(X), & \text{else} \end{cases} \quad (1)$$

The local cost $L(X)$ of a non-ROI voxel is given by:

$$L(X) = \begin{cases} 1, & \text{if } f_G(X) = 1 \\ 1, & \text{if } f_V(X) = 1 \\ wf_G(X) + (1-w)f_V(X), & \text{else.} \end{cases} \quad (2)$$

The function $fG(X)$ determines the component of the cost based solely on the voxel's HU value, $fV(X)$ is a "valley" cost enforcing the requirement that an airway voxel is should be less than the surrounding airway walls and determines the relative weighting given to each.

The gray-scale HU cost $fG(X)$ enforces the fact that airway voxels must have small HU values, $$f_G(X) = \begin{cases} 0, & \text{if } I(X) \leq -1000 \\ \left(\frac{I(X)+1000}{T+1000}\right)^2, & \text{if } -1000 < I(X) \leq T, \\ 1, & \text{if } T < I(X) \end{cases} \quad (3)$$

$I(X)$ is the gray-scale value of the image volume at a location X and T is the maximum gray-scale threshold for voxels to be considered air and is nominally set to a value of −750HU.

Figure 5:
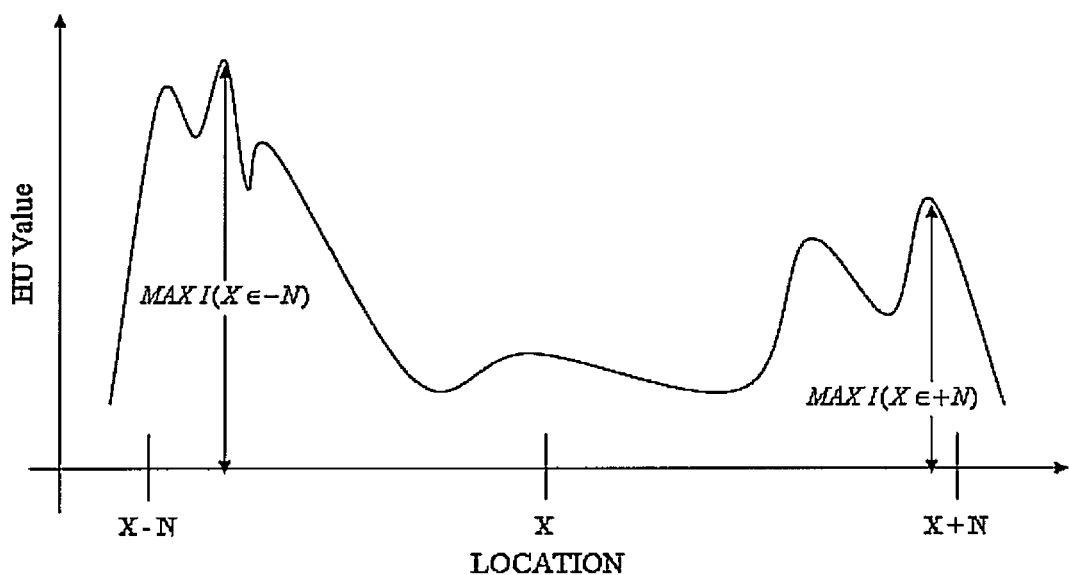
FIG. 5 shows the value of search distance N in one dimension.

The function $fV$ is the median "valley" cost which enforces that the value of an airway voxel must be smaller than those in its neighborhood. As an intermediate step, the value $$f_{MED}(X) = MED \begin{pmatrix} \text{MIN}(\text{MAX}(I(X \in N_x^-), I(X \in N_x^+))), \\ \text{MIN}(\text{MAX}(I(X \in N_y^-), I(X \in N_y^+))), \\ \text{MIN}(\text{MAX}(I(X \in N_z^-), I(X \in N_z^+))) \end{pmatrix} - I(X) \quad (4)$$

is computed. Equation 4 determines if a voxel at X is smaller than its neighbors, where N is the search distance along a direction x,y,z. In one dimension, this value is illustrated in FIG. 5. MAX $I(X \in N^+)$, as the minimum of the maxima on either side of the voxel at location X, is the valley cost for this dimension.

The median value is then linearly scaled by the function $$f_V(X) = \begin{cases} 1, & \text{if } f_{MED}(X) < T_L \\ \frac{1}{T_L - T_H}(f_{MED}(X) - T_H), & \text{if } T_L \leq f_{MED}(X) \leq T_H \\ 0, & \text{if } T_H < f_{MED}(X) \end{cases} \quad (5)$$

The values TL and TH are the upper and lower thresholds that determine the range of acceptable valley-cost values.

Connected Set Determination

Path-extensions are determined by constructing a graph where each voxel in the medical image is a vertex with edges connecting each voxel to its 26-connected neighbors. A directed edge weight $E(U,V)$ from a voxel at location U to one at location V is determined by $$E(U,V) = |U-V|C(V), \quad (6)$$

the distance between the voxel locations scaled by the voxel cost for the voxel at location V.

Smooth 3D Locations and Determine Viewing Directions

The output of Algorithm 3 is typically jagged. Smoothing these locations yields path extensions that are more visually appealing. The smoothing is accomplished by fitting sets of line segments, the endpoints of which are defined by combinations of voxels, each at a location (UJ), within the jagged connected set (J). The best set of end points (S) is that which minimizes the total error (E) given by:

$$E = \sum_{U_J \in J} (a|U_J - Proj(U_J, S)|^2 + SL(Proj(U_j, S))). \quad (7)$$

which is the sum of the squared distance between the voxels in the connected set and their projection onto the line segments defined by S scaled by a weighting factor and the gray-scale cost of the projection of the point scaled by another weighting factor. By defining the error in this manner, the projections of the voxels in the connected set must be geometrically near the original voxels as well as in locations that have the local appearance of airway voxels.

Method 5: Incorporate Procedure-Specific Navigation Directions

This method modifies the orientation of each view site to reflect a desired procedure or visualization. Two orthogonal sets of directions are calculated at each view site: the tangential viewing direction and the up direction. The tangential viewing directions are computed using Kiraly's method so that each view site faces the end of its branch.[20] This method linearly blends the first N tangential viewing directions on a branch with the tangential viewing direction at the last view site on the previous (parent) branch to avoid abrupt tangential viewing direction changes at bifurcations. To determine the up direction at each site, Kiraly's method selects an up vector at the root which is projected from site to site along each path. Each projection seeks to minimize the change in the up direction between contiguous sites while satisfying the constraint that the up vectors must be orthogonal to the tangential vectors.

Our procedure-specific navigation directions modify the arbitrarily-defined up vectors to correspond with the orientation of the endoscopic device during a procedure. Often, the up direction is dependent upon the relative orientation of the next branch (the child, bC) to be encountered along a route as compared to the current branch (the parent, bP). Each branch has a direction vector, $\vec{C}$ and $\vec{P}$, respectively. $\vec{C}$ and $\vec{P}$ are oriented at the first view site on their branches and point toward the last view site on their branch. By convention, $\vec{C}$ and $\vec{P}$ are unit vectors. We use these directions to determine the up vector, $\vec{U}$ and the tangential vector, $\vec{T}$, also unit vectors, with $\vec{U}$ orthogonal to $\vec{T}$ at each view site. The orthogonality constraint requires the up vector to lie in the plane whose normal is given by $\vec{T}$. To determine procedure-specific viewing directions, the projection is denoted by $\vec{R}$. Because the orientation of the device is often dependent upon the orientation of the next branch, by calculating $\vec{R}$, the viewing directions can be constructed so that up vector at the final site is oriented in any desired position relative to $\vec{R}$. $\vec{R}$ is determined by:

$$\vec{R} = -((\vec{P} \times \vec{C}) \times \vec{P}). \quad (8)$$

The view site is then determined by setting $\vec{U}$ and $\vec{T}$ such that $\vec{U}$'s relative orientation compared to $\vec{R}$ abides by the rules for the route. In the example that requires the child branch to be at the top of the view, the rule would be that for the last view site on the branch $\vec{R} = \vec{U}$.

The up vectors can change quite drastically along a route to follow the procedure-specific rules. Using the previously described "always-up" rule, there can be 180 degree of roll between closely-spaced branches. To reflect the fact that endoscopic devices generally move smoothly, the up vectors between branches are linearly blended in a manner similar to the tangential vectors.

Route-Planning Implementation

Figure 6:
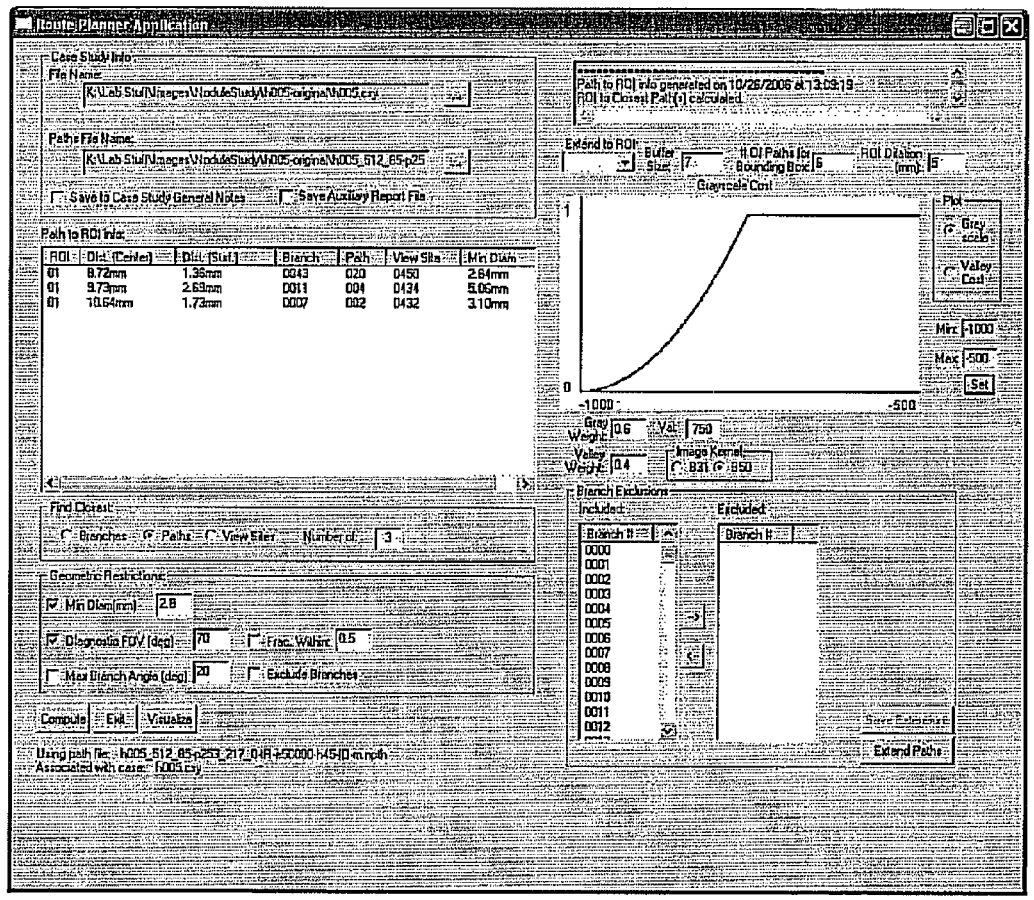
FIG. 6 is a view of the route-planning computer program.
Figure 7:
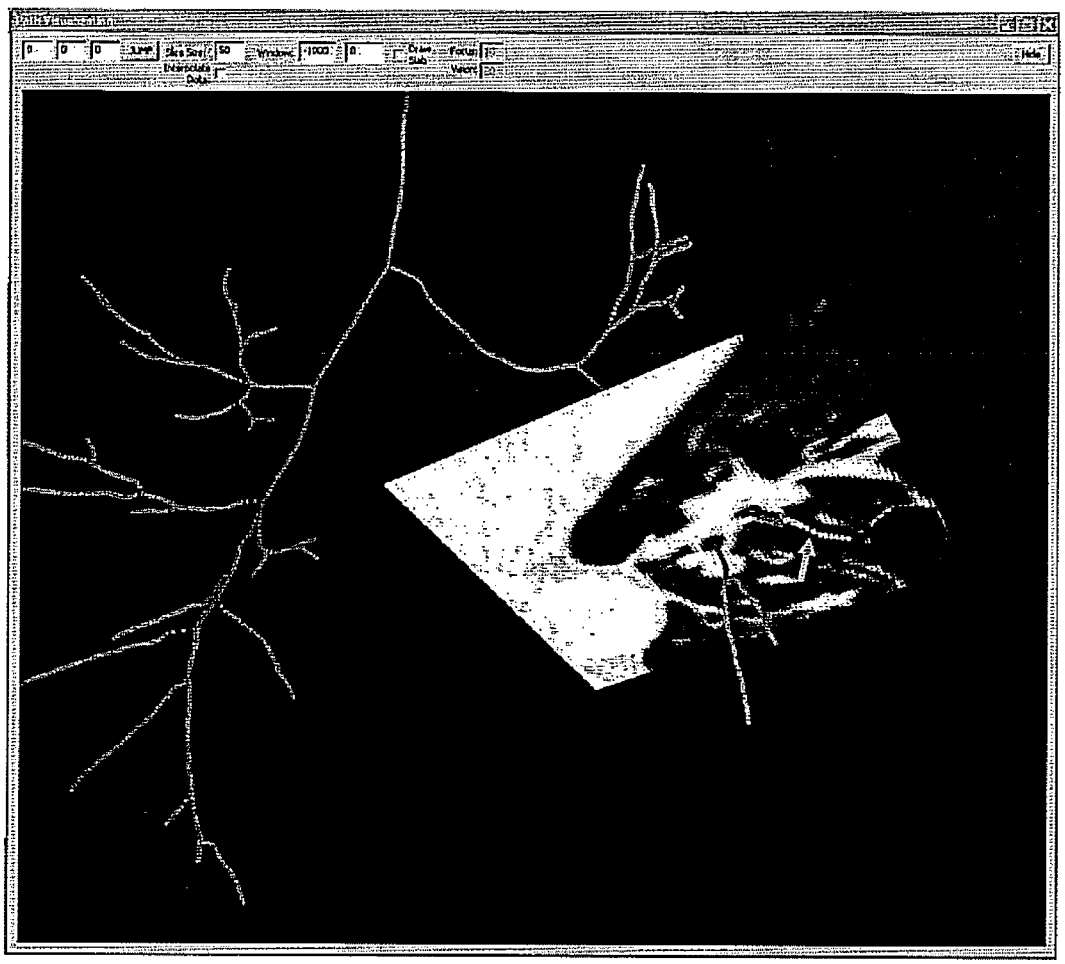
FIG. 7 is a different view of the route-planning computer program.
Figure 8A:
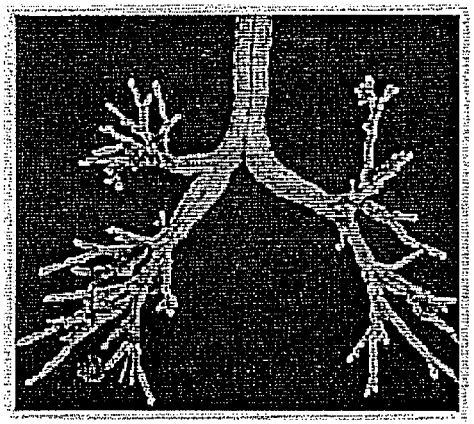
FIG. 8A shows a view the route in a surface rendered view.
Figure 8B:
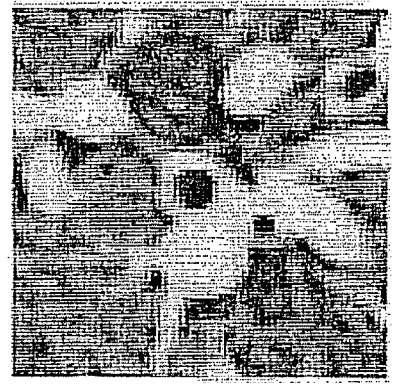
FIG. 8B shows the CT data at this location where the airway diameter is 4.1 mm.
Figure 8C:
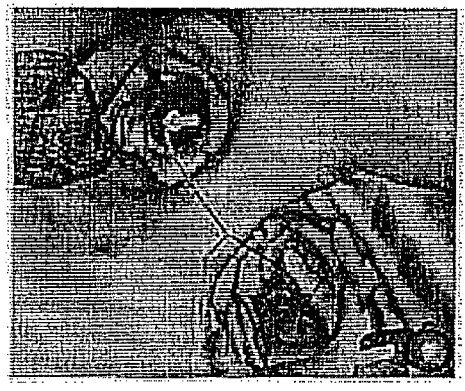
FIG. 8C shows an endoluminal view of the airway surface and ROI near the route destination.
Figure 8D:
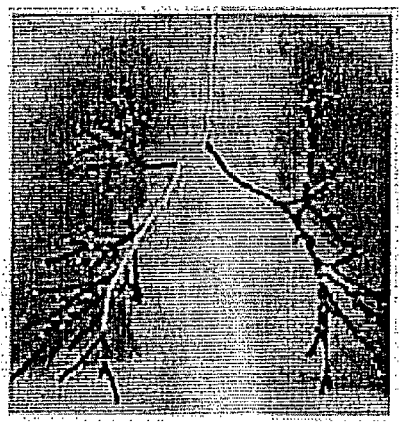
FIG. 8D shows a weighted-sum coronal projection of the CT data with the paths, route and the ROI.

Views of the route-planning computer program are shown in FIGS. 6 and 7. In this part of the program, the user can input the various device and procedure constraints. Finding the acceptable routes within the input tree as in Methods 1 and 2 is nearly instantaneous. Upon completing these calculations, the destinations of the closest-routes are displayed and optionally saved to a file. The left half of the application displays the inputs and outputs for Methods 1 and 2. The user loads a case study which includes the 3D MDCT image, the voxels to which the ROI belongs, and a paths file containing the view sites of the airway tree. The user inputs the number of closest routes on separate airway-tree segments to be found for each ROI in the "Find Closest" section. The "Geometric Restrictions" section contains the inputs for the device and procedure constraints. The results of Methods 1 and 2 are displayed in the "Path to ROI" section. The right half of the application shows details related to Method 3. The amount of ROI dilation is entered in "ROI Dilation (mm)." The plot gives a visual representation of the functions of each component of the cost function. The user can change the upper limit on the gray-scale cost (shown at its default of −750) and the relative weighting given to the gray-scale and valley costs. The results of the path extension are displayed in FIG. 7. If these results are deemed accurate and appropriate for the procedure, the user can append the extensions to the original paths (centerlines) file.

In the event that the routes determined by Methods 1 and 2 are inadequate, Method 3 is used to extend the existing paths. Method 3 usually requires a few seconds (minimum 0.5 sec to maximum 15 sec in cases inspected to date) to complete its calculations. After performing path extensions, the application includes a 3D visualization for viewing the original paths, ROIs, path extensions, and 3D image data. This is shown in FIG. 7. The user can dynamically interact with the scene by changing the 3D viewing position and can choose which structures to display: the airway tree, any arbitrary slice of the 3D volumetric image (the black and white square), path extensions, or the ROI. By examining the different the slices of the 3D medical data through which the extended paths travel, the correctness of extensions is easily verified. The user can use the mouse to look at the scene from any viewing location in 3D space. Arbitrary slices of the 3D volumetric image can be overlayed on the path extensions and ROI so that the user can visually inspect the correctness of the route in the volumetric medical image. If the route is incorrect, the user can change parameters in the part of the program shown in FIG. 6, including changing the amount of ROI dilation and the branches from which extensions are allowed. Once an acceptable path extension is found, the user can append the extension to the file containing the centerline locations.

RESULTS

We evaluated the performance of the route-planning methods in 10 human CT cases. The MDCT data were collected from a Philips Mx8000 four-detector scanner and a Siemens Sensation-16 sixteen-detector scanner. Suspect ROIs, consisting of nodules and infiltrates located in the lung periphery, were defined by a physician using the 3D live-wire technique.

A summary of the test cases is given in Table I, with the results of our automated route-planning method outlined in Table II.

Figure 9A:
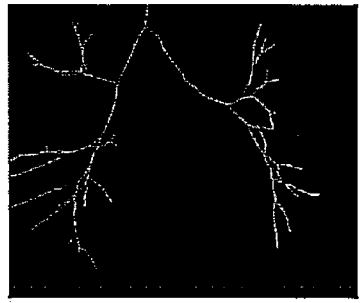
FIG. 9A shows a 3D representation of the centerlines, extension and ROI.
Figure 9B:
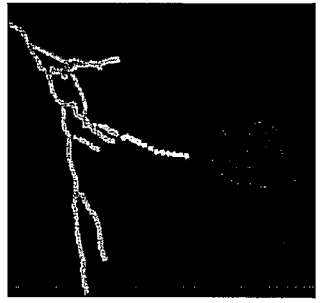
FIG. 9B is a close-up of the view of FIG. 9A.
Figure 9C:
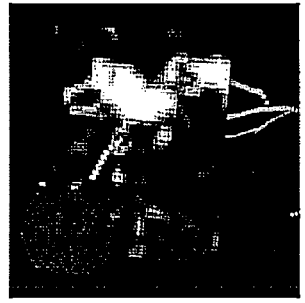
FIG. 9C shows a close-up view of the ROI, centerlines, and extension as well as a slice through which the extension traverses.

For these results, routes are sought that terminate within 30 mm of the target ROI. Method 1 is first used to determine if such routes exist within the original organ tree T. An example of such a case is given in FIGS. 8A through 8D. In the upper left view shows the route in a surface rendered view. The route terminates 16.9 mm from the ROI surface. The sphere shows the route's terminal location with the line segment showing the viewing direction at this location. The upper right view shows the CT data at this location where the airway diameter is 4.1 mm. The bottom-left endoluminal view provides a virtual view of the airway surface and ROI near the route destination (arrow). The route destination appears as a fixed-sized arrow in the endoluminal view, the appearance of which, in the 3D perspective view, gives the notion of how far away the current location is from the destination. The arrow points to the ROI center-of-mass, providing an additional 3D cue as to the relative locations of the ROI, current viewing position, and route destination. The bottom-right view is a weighted-sum coronal projection of the CT data with the paths, route and the ROI. If no such route exists, Method 3 or Method 4 finds a path extension. By using these methods, acceptable routes are found to every ROI. Method 3 was used to extend the routes in case 21405.3a. Method 4 was used to extend paths from locations with a minimum diameter of 1.5 mm in case b004. FIGS. 9A to 9C depict a route containing a path extension with a 3D view of the existing centerline locations, the ROI, the path extension and a slice of the 3D data through which the extension is defined. The image shown in FIG. 9A is a 3D representation of the centerlines, extension and ROI. The image shown in FIG. 9B is a close-up of the same view. The image shown in FIG. 9C shows a close-up view of the ROI, centerlines, and extension as well as a slice through which the extension traverses. This slice show representations of the CT volume at the location on the extended branch shown in the coronal projection view on the right. The middle-top image displays an oblique cross-section of the volume with a viewing direction oriented tangentially to the extended path. The middle-bottom image shows an endoluminal rendering of the data set as viewed in the same direction. The length of the path extension is 28.1 mm.

Table I is a summary of the images used in the evaluation of the route-planning method. ROI location describes the lung lobe (R)ight, (L)eft, (U)pper, (M)iddle, (L)ower in which the ROI is defined.

TABLE I

| Patient ID | Scanner | Number of Slices | Axial-Plane Resolution(mm) | ROI Location |
|---|---|---|---|---|
| b001 | Siemens | 193 | 0.55 | RUL |
| b004 | Siemens | 338 | 0.81 | RUL |
| b005 | Siemens | 308 | 0.73 | LLL |
| b001-2 ROIs | Philips | 414 | 0.57 | RLL |
| h002 | Philips | 515 | 0.59 | LLL |
| h005 | Philips | 479 | 0.59 | RML |
| h013 | Philips | 539 | 0.76 | RLL |
| h019 | Philips | 597 | 0.74 | LLL |
| p2h038 | Philips | 410 | 0.67 | LUL |
| 21405.3a | Siemens | 706 | 0.67 | RML |

Table II shows a summary of results of route planning to ROIs located in the lung periphery using Methods 1 and 3. For those cases where path extension (Method 3 or Method 4) is necessary, results are shown (before, after) the path extension. Using a 30 mm maximum allowable distance from the route's terminal location, the method yields adequate routes to all ROIs investigated (column 3).

TABLE II

Figure 10:
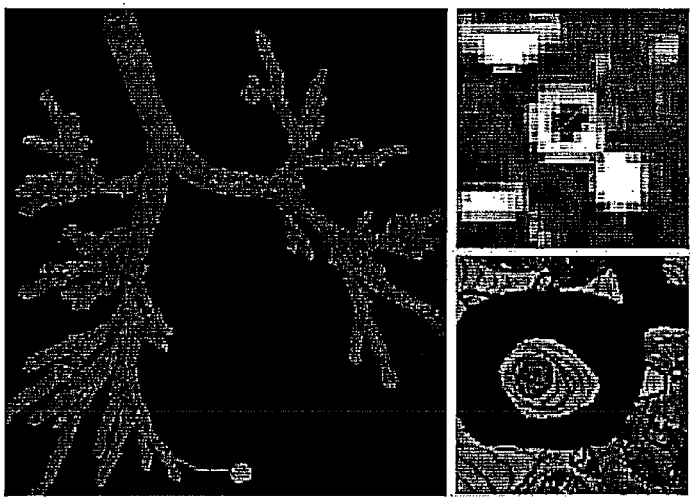
FIG. 10 shows a different visual representation of a route with an extended path to reach a peripheral lung nodule ROI.

| Patient ID | ROI in Airway | Distance from Route Termination to ROI (mm) | Method 3 Necessary? | Number of Airway Generations | Terminating Airway Diameter (mm) |
|---|---|---|---|---|---|
| b001 | No | 16.5 | No | 5 | 2.8 |
| b004 | No | 42.4, 29.2 | Yes | 5, 8 | 3.3, 1.5 |
| b005 | No | 18.0 | No | 6 | 2.8 |
| h001 - ROI 1 | No | 28.3 | No | 8 | 2.1 |
| h001 - ROI 2 | No | 17.7 | No | 9 | 2.3 |
| h002 | Yes | 0.0 | No | 6 | 3.2 |
| h005 | Yes | 0.0 | No | 5 | 4.8 |
| h013 | No | 12.3 | No | 6 | 3.1 |
| h019 | No | 28.3 | No | 5 | 3.7 |
| p2h038 | No | 27.9 | No | 8 | 1.8 |
| 21405.3a | No | 35.9, 28.3 | Yes | 8, 9 | 2.2, 1.4 | clearly shows an airway that was missed during the initial segmentation and may provide an adequate route to the ROI. The 3D MDCT image size is 512×512×596 with $\Delta x = \Delta y = 0.74$ mm, $\Delta z = 0.60$ mm (case h019). FIG. 10 shows an integrated set of views of a path extended to reach a peripheral lung nodule ROI. The 3D MDCT image size is 512×512×414 with $\Delta x = \Delta y = 0.57$ mm, $\Delta z = 0.60$ mm (case h001). The leftmost view shows the extended path in a surface rendered view. Previously existing paths display both centerlines and a rendering of the segmented airway while the extended path only shows the centerline. The middle views The results presented in Table III show how utilizing device constraints in Method 2 may yield different routes than those previously determined. In the table, the constraint on the minimum path diameter is chosen to be 2.8 mm in most instances, reflecting the diameter of currently available ultra-thin bronchoscopes. A diagnostic field of view of either 180 degrees, which essentially eliminates this constraint or 70 degrees, a more exacting standard, is required at terminal route locations. When taking into account these device constraints, routes do not exist to all target ROIs when using the same 30 mm cutoff as before.

TABLE III

| Patient ID | Endoscope Diameter Input (mm) | Diagnostic FOV Input (deg) | Distance (mm) from Route Termination | Number of Airway Generations | Minimum Airway Diameter Encountered (mm) |
|---|---|---|---|---|---|
| b001 | 2.8 | 180 | 23.1 | 4 | 3.5 |
| b005 | 2.8 | 180 | 34.7 | 5 | 3.6 |
| b005 | 2.4 | 70 | 32.0 | 6 | 2.4 |
| h001 - ROI 1 | 2.8 | 70 | 69.6 | 6 | 6.1 |
| h001 - ROI 1 | 2.8 | 180 | 38.0 | 9 | 2.9 |
| h001 - ROI 2 | 2.8 | 70 | 16.9 | 9 | 4.1 |
| h002 | 2.8 | 70 | 4.7 | 6 | 2.8 |
| h005 | 2.8 | 70 | 1.4 | 5 | 2.8 |
| h0013 | 2.8 | 70 | 24.4 | 6 | 2.8 |
| h019 | 2.8 | 70 | 28.7 | 5 | 3.7 |
| p2h038 | 2.8 | 70 | 46.3 | 5 | 3.0 |
| p2h038 | 2.8 | 180 | 36.4 | 6 | 3.0 |

Figure 11A:
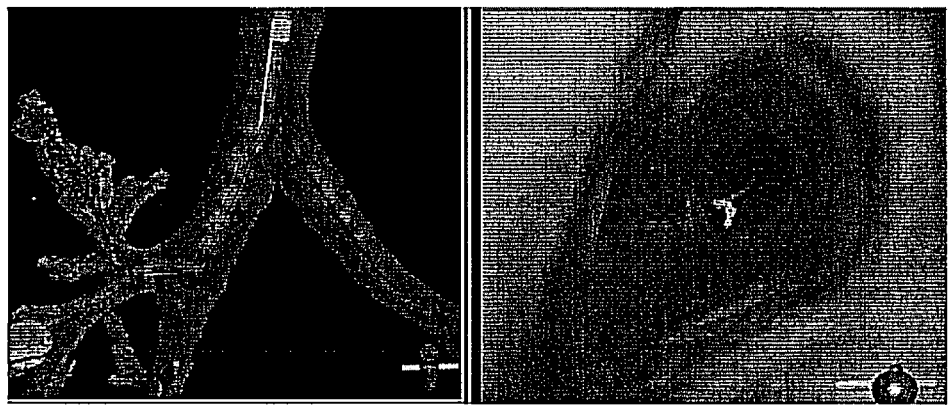
FIGS. 11A through 11H show how the view directions may be modified to reach an ROI in the anterior segment of the right upper lobe of the lung.
Figure 11B:
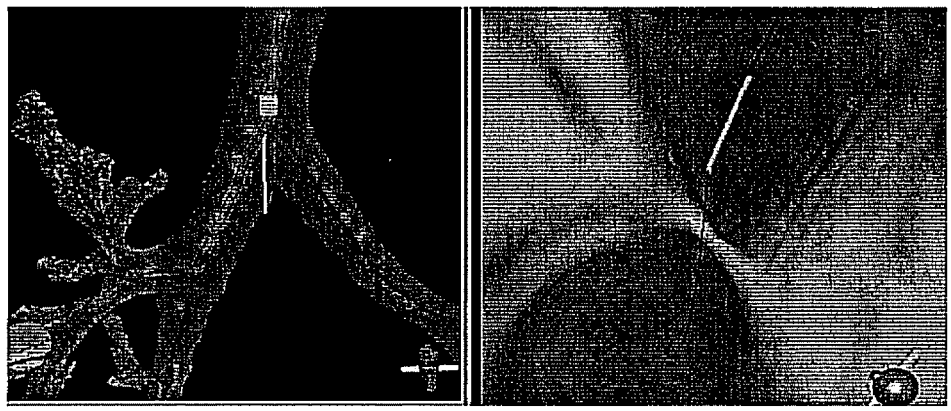
Figure 11C:
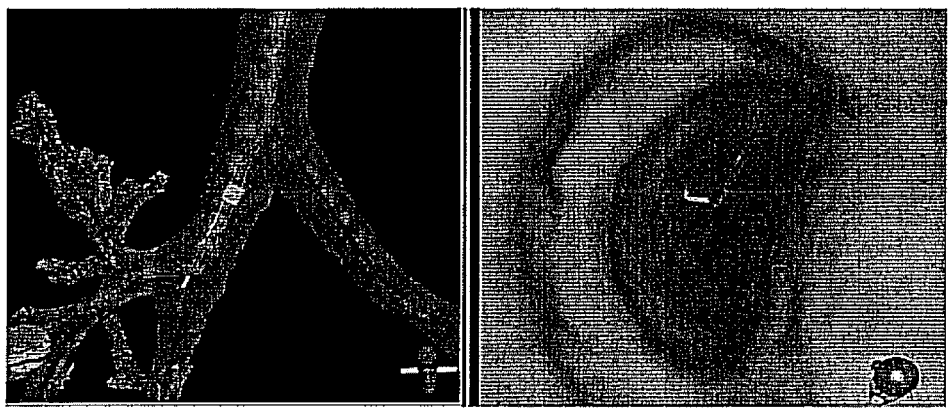
Figure 11D:
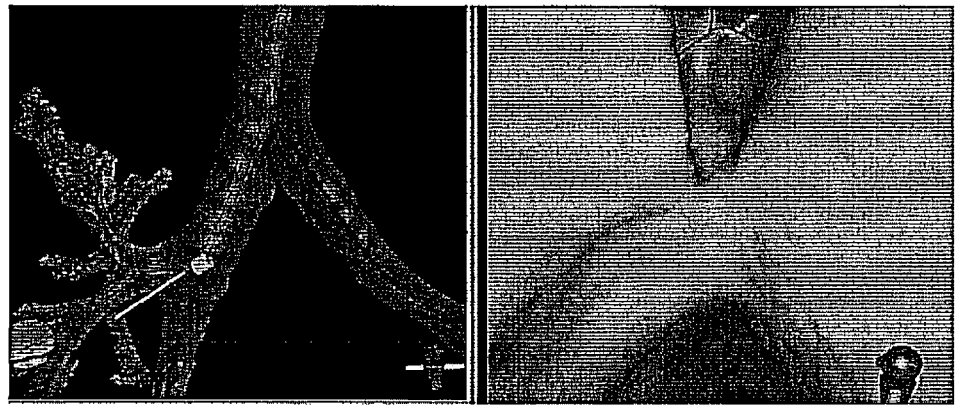
Figure 11E:
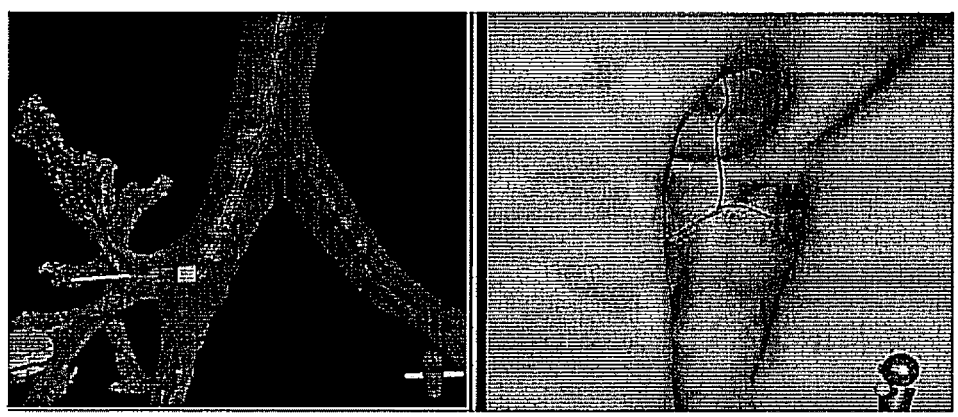
Figure 11F:
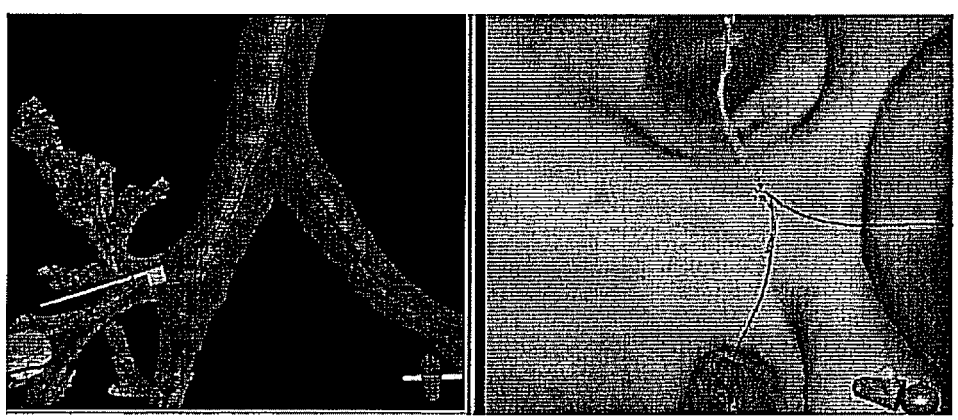
Figure 11G:
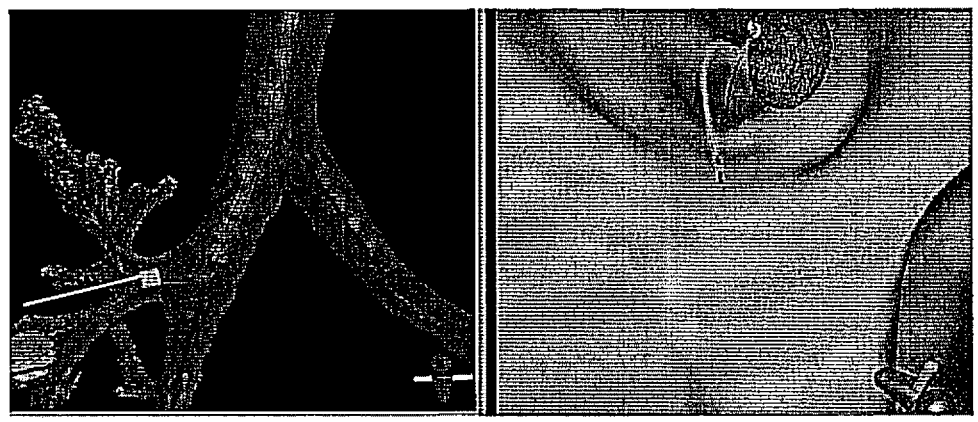
Figure 11H:
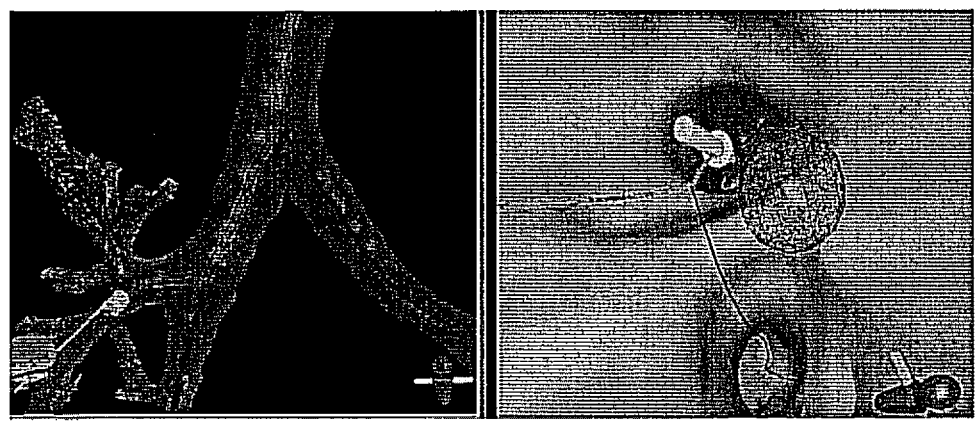

FIGS. 11A-H illustrates how the view directions are modified by Method 5 to reach an ROI in the anterior segment of the right upper lobe of the lung. In this example, view directions are chosen so that each viewing site faces the end of the branch to which it belongs and the next branch along the route is up (oriented at the top of the view) by the end of the current branch. Starting at FIG. 11A, the viewing location is in the main carina. In FIG. 11B, the scene is rotated so the right main bronchus appears in the top of the view. In FIG. 11C, the right-upper-lobe takeoff is seen in the distance. In FIG. 11D, the right-upper-lobe takeoff has been oriented toward the top of the view. Continuing down the right upper lobe bronchus in FIG. 11E, the trifurcation into the anterior, posterior, and apical segments is seen in the distance. As the trifurcation gets nearer, in FIG. 11F, the view is rotated so the posterior segment is toward the top of the view. In FIG. 11G, the ROI and route destination (arrow) are seen in the distance. In FIG. 11H, the route destination and ROI are nearly reached. The ROI surface is located at a distance of 12 mm from the final route destination.

We claim:

1. A method of planning routes through a 3D image of a tubular organ prior to an actual, follow-on endoscopic procedure, said organ being in the chest region, said method comprising the steps of:
    computing a model of an airway tree from 3D image data of the organ;
    receiving information about a target region of interest (ROI) and the follow-on endoscopic procedure associated with the organ;
    deriving at least one anatomical constraint, at least one endoscopic-device constraint, and at least one procedure-specific constraint from said information,
    wherein the deriving step comprises constructing a geometric field of view of a virtual endoscope, and requiring at least a portion of the target region of interest (ROI) to be within the geometric field of view extending from the virtual endoscope;
    automatically computing a plurality of navigable routes to the target region of interest (ROI) and enabling at least one of said routes to be selected based on said anatomical, endoscopic-device, and procedure-specific constraints derived from the information received; and
    displaying said at least one selected route in conjunction with said model.

2. The method of claim 1, wherein said ROI is outside of said airway, said method including the step of extending the route from within the airway to the ROI.

3. The method of claim 1, including the step of automatically calculating a viewing direction at each site along the route to give navigation directions.

4. The method of claim 1, wherein the information includes locations to avoid.

5. The method of claim 1, wherein the information includes locations to be included along said route.

6. The method of claim 1, wherein the information includes a metric for selecting the route.

7. The method of claim 6, wherein the metric is a minimum distance to the ROI such that the route satisfies the constraints.

8. The method of claim 1, wherein the information further includes details of the ROI.

9. The method of claim 1, wherein the information includes the central axes of the airway tree, and a minimum diameter of the airways.

10. The method of claim 1, wherein the information includes a parametric description of the endoscopic device.

11. The method of claim 10, wherein the parametric description includes the diameter, and flexibility of the endoscopic device.

12. The method of claim 10, wherein the parametric description includes a detail of an ancillary tool used in conjunction with the endoscopic device.

13. The method of claim 12, wherein said ancillary tool is a needle.

14. The method of claim 1, wherein the ROI is a nodule.

15. The method of claim 1, wherein the information is at least in part derived from said 3D image data, and said image data is obtained through a multidetector computed tomographic (MDCT) chest image.

16. The method of claim 1 wherein the follow-on procedure comprises a bronchoscopy procedure, and said information comprises a size of a bronchoscope, and a maximum bending angle of the bronchoscope.

17. The method of claim 1 wherein the geometric field of view is cone-shaped.

18. The method of claim 1 wherein the geometric field of view is a diagnostic field of view.

19. A method of planning an endoscopic route through an organ having a lumen prior to an actual, follow-on endoscopic procedure, said method comprising the steps of:
    providing anatomical and parametrical information about the organ, the follow-on endoscopic procedure and a target region interest (ROI) positioned outside of said lumen;
    automatically computing at least one entire route beginning at a base of the organ to a route destination within said lumen which is near said ROI using the information provided; and automatically computing an extension from said route destination to said ROI, where the extension comprises a plurality of view sites connected to said route destination within said lumen; and wherein said view sites are determined prior to the follow-on procedure based on the information provided.

20. The method of claim 19, wherein the information includes locations to avoid along the route.

21. The method of claim 19, wherein the information includes locations to be included along the route.

22. The method of claim 19, wherein the at least one route includes a plurality of routes, and said information includes a metric for selecting a first route.

23. The method of claim 22, wherein the metric is a minimal distance to the ROI.

24. The method of claim 19, wherein the information comprises data about the ROI.

25. The method of claim 19, wherein the information includes central axes of the organ, and minimum diameter of the lumen.

26. The method of claim 19, wherein the information includes a parametric description of the endoscopic device.

27. The method of claim 26, wherein the parametric description includes at least one of the diameter, and flexibility of the endoscopic device.

28. The method of claim 26, wherein the parametric description includes a detail of an ancillary device of said follow-on procedure.

29. The method of claim 19, wherein the organ is a branching organ.

30. The method of claim 19, wherein the organ is an airway tree.

31. The method of claim 19, wherein the information is derived at least in part from 3D image data of a lung, and said image data is obtained through a multidetector computed tomographic (MDCT) chest image.

32. A system for planning routes through an organ prior to an actual, follow-on endoscopic procedure, said organ comprising a lumen having a wall and at least one region of interest [ROI], said system comprising:

a memory for storing information about the organ and the follow-on endoscopic procedure associated with the organ, said information including anatomical, endoscopic-device, and procedure-specific constraints requiring at least a portion of the ROI to be within a geometric field of view of a virtual endoscope, said field of view extending beyond a wall of said lumen; and a processor operative to perform the following functions prior to the actual procedure:
  a) access the stored information and automatically determine at least one route destination along said lumen and in close proximity to the ROI to automatically determine at least one complete route through the organ from a base of the organ to the route destination for performing said follow-on endoscopic procedure given said constraints, and
  b) send said at least one complete route to a display device for presentation of said route on the display device in conjunction with a 3D image of the organ.

33. The system of claim 32, wherein the ROI is outside of the lumen, and said processor is further operative to determine an extension from said route destination to said ROI.

34. The system of claim 32, wherein the processor is further operative to modify the viewing direction at each site along said route to give navigation directions.

35. The system of claim 32 wherein the stored information includes locations to avoid.

36. The system of claim 32, wherein the stored information includes locations to be included within said route.

37. The system of claim 32, wherein the stored information includes a metric for selecting the route.

38. The system of claim 37, wherein the metric is the minimal distance to the ROI from the route destination.

39. The system of claim 32, wherein the stored information includes details about the ROI.

40. The system of claim 32, wherein the stored information includes the central axes of the lumen, and the diameter of the lumen.

41. The system of claim 32, wherein the stored information includes a parametric description of the endoscopic device.

42. The system of claim 41, wherein the parametric description includes at least one of the diameter, and flexibility, of the endoscopic device.

43. The system of claim 41, wherein the parametric description includes details of an ancillary tool used in conjunction with the endoscopic device.

44. The system of claim 32, wherein the stored information is derived at least in part from 3D image data of a lung, and said image data is obtained through a multidetector computed tomographic (MDCT) chest image.

* * * * *